(12) United States Patent
Kansal et al.

(10) Patent No.: US 7,470,812 B2
(45) Date of Patent: Dec. 30, 2008

(54) CHIRAL 3-CARBAMOYLMETHYL-5-METHYL HEXANOIC ACIDS, KEY INTERMEDIATES FOR THE SYNTHESIS OF (S)-PREGABALIN

(75) Inventors: Vinod Kumar Kansal, Haryana (IN); Brijnath P. Chaurasia, Uttar Pradesh (IN); Anand Prakash Tiwari, Uttar Pradesh (IN)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/894,855

(22) Filed: Aug. 21, 2007

(65) Prior Publication Data

US 2008/0051602 A1 Feb. 28, 2008

Related U.S. Application Data

(62) Division of application No. 11/523,865, filed on Sep. 19, 2006.

(60) Provisional application No. 60/839,947, filed on Aug. 23, 2006, provisional application No. 60/763,696, filed on Jan. 30, 2006, provisional application No. 60/763,593, filed on Jan. 30, 2006, provisional application No. 60/754,392, filed on Dec. 27, 2005, provisional application No. 60/753,220, filed on Dec. 21, 2005, provisional application No. 60/752,434, filed on Dec. 20, 2005, provisional application No. 60/718,689, filed on Sep. 19, 2005.

(51) Int. Cl.
C07C 205/00 (2006.01)
C12P 13/00 (2006.01)
C07D 211/20 (2006.01)
C07F 7/04 (2006.01)

(52) U.S. Cl. ................. 562/553; 435/128; 546/248; 558/441

(58) Field of Classification Search .................. 562/553
See application file for complete search history.

(56) References Cited

U.S. PATENT DOCUMENTS

| | | | |
|---|---|---|---|
| 5,010,189 A | 4/1991 | Herold et al. | |
| 5,599,973 A | 2/1997 | Silverman et al. | |
| 5,616,793 A | 4/1997 | Huckabee et al. | |
| 5,629,447 A | 5/1997 | Huckabee et al. | |
| 5,637,737 A | 6/1997 | Andres et al. | |
| 5,637,767 A | 6/1997 | Grote et al. | |
| 6,001,876 A | 12/1999 | Singh | |
| 6,197,819 B1 | 3/2001 | Silverman et al. | |
| 6,333,198 B1 | 12/2001 | Edmeades et al. | |
| 6,488,964 B2 | 12/2002 | Bruna et al. | |
| 6,580,003 B2 | 6/2003 | Deng et al. | |
| 6,924,377 B2 | 8/2005 | Blazecka et al. | |
| 7,141,695 B2 | 11/2006 | Przewosny et al. | |
| 2001/0016665 A1 | 8/2001 | Grote et al. | |
| 2003/0212290 A1 | 11/2003 | Burk et al. | |
| 2003/0225149 A1 | 12/2003 | Blazecka et al. | |
| 2005/0222464 A1 | 10/2005 | Hoge, II | |
| 2005/0228190 A1 | 10/2005 | Bao et al. | |
| 2005/0283023 A1 | 12/2005 | Hu et al. | |
| 2006/0270871 A1 | 11/2006 | Khanduri et al. | |
| 2007/0073085 A1 | 3/2007 | Hedvati et al. | |
| 2008/0014280 A1 | 1/2008 | Kumar et al. | |

FOREIGN PATENT DOCUMENTS

| | | |
|---|---|---|
| CN | 1 634 869 | 7/2005 |
| CZ | 297 970 | 3/2007 |
| WO | WO 96/38405 A1 | 12/1996 |
| WO | WO 96/40617 A1 | 12/1996 |
| WO | WO 01/55090 A1 | 8/2001 |
| WO | WO 2006/000904 A2 | 1/2005 |
| WO | WO 2005/100580 | 10/2005 |
| WO | WO 2006/008640 | 1/2006 |
| WO | WO 2006/136087 | 12/2006 |
| WO | WO 2008/004044 | 1/2008 |
| WO | WO 2008/007145 | 1/2008 |
| WO | WO 2008/009897 | 1/2008 |

OTHER PUBLICATIONS

Berner et al. "Asymmetric Michael Additions to Nitroalkenes", *European Journal of Organic Chemistry*, 1877-1894 (2002).
Cason et al., "Branched-Chain Fatty Acids. XXVII. Further Study of the Dependence of Rate of Amide Hydrolysis on Substitution near the Amide Group. Relative Rates of Hydrolysis of Nitrile to Amide and Amide to Acid", *J. Org. Chem.*, 18(9): 1129-1136 (1953).
Chen et al., "Synthesis of Pregabalin", *Zhongguo YiYao Gongye Zazhi*, 35(4):195-196 (2004).
Colonge et al., "Preparation De Pyrrolidones-2 et de Gamma-Aminoacides", *Bulletin De La Societe Chimique De France, Societe Francaise De Chimie*, 598-603 (1962).
Day and Thorpe, "The Formation and Reactions of Imino-compounds. Part XX. The Condensation of Aldehydes with Cyanoacetamide", *J. Chem. Soc.*, 117: 1465-1474 (1920).
Hoekstra et al., "Chemical Development of CI-1008, an Enantiomerically Pure Anticonvulsant", *Organic Process Research and Development*, 1(1):26-38 (1997).
Karanewsky et al., "Practical Synthesis of an Enantiomerically Pure Synthon for the Preparation of Mevinic Acid Analogues", *J. Org. Chem.*, 56(11):3744-3747 (1991).
Shintani et al., "Highly Enantioselective Desymmetrization of Anhydrides by Carbon Nucleophiles: Reactions of Grignard Reagents in the presence of (-)-Sparteine", *Angewandte Chemie, International Edition*, 41(6): 1057-1059 (2002).
Snyder et al., Introduction To Modern Liquid Chromatography, 549-572 (2nd Ed., John Wiley & Sons, Inc., 1979).
Strobel et al., Chemical Instrumentation: A Systematic Approach, 391-393, 879-894, 922-925, 953 (3rd Ed., 1989).

(Continued)

*Primary Examiner*—Daniel M Sullivan
*Assistant Examiner*—Louisa Lao
(74) *Attorney, Agent, or Firm*—Kenyon & Kenyon LLP

(57) ABSTRACT

The invention encompasses the synthesis of (S)-(+)-3-(aminomethyl)-5-methylhexanoic acid, (S)-Pregabalin, via the intermediate, (3R)-5-methyl-3-(2-oxo-2{[(1R)-1-phenylethyl]amino}ethyl)hexanoic acid.

86 Claims, 4 Drawing Seets

OTHER PUBLICATIONS

Theisen et al., "Prochiral Recognition in the reaction of 3-Substituted Glutaric Anhydrides with Chiral Secondary Alcohols," *J. Org. Chem.*, 58(1): 142-146 (1993).

Verma et al., "Desymmetrization of prochiral anhydrides with Evans' oxazolidinones: and efficient route to homochiral glutaric and adipic acid derivatives", *Journal of the Chemical Society, Perkin Transactions 1: Organic and Bio-Organic Chemistry*, 257-264 (1999).

Martin et al. "Pregabalin: CI-1008, PD-144723" Drugs of the Future, vol. 24, No. 8, pp. 862-870, (1999).

Yamamoto et al., "Stereoselective Synthesis of (E)-Alkylidenesuccinates by Palladium-catalyzed Carbonylation", Bull.Chem.Soc.Japan., vol. 58, pp. 3397-3398 (1985).

G. M. Sammis et al., "Highly enantioselective catalytic conjugate addition of cyanide to a,β-unsaturated imides", J.Am.Chem.Soc., vol. 125, No. 15, pp. 4442-4443 (2003).

Andruszkiewicz and Silverman, "A convenient synthesis of 3-Alkyl-4-aminobutanoic acids", Synthesis, pp. 953-955 (1989).

H. Li, et al., "Highly enantioselective catalytic conjugate addition of malonate and β-ketoester to nitroalkenes: asymmetric C-C bond formation with new bifunctional organic catalysts based on cinchona alkaloids", J. Am. Chem. Soc., vol. 126, No. 32, pp. 9906-9907 (2004).

D.M. Barnes, et al., "Development of a Catalytic Enantioselective Conjugate Addition of 1,3-Dicarbonyl Compounds to Nitroalkenes for the Synthesis of Endothelin-A Antagonist ABT-546, Scope, Mechanism, and Further Application to the Synthesis of the Antidepressant Rolipram", J. Am.Chem.Soc., vol. 124, No. 44, pp. 13097-13105 (2002).

T. Okino, et al., "Entantio- and Diastereoselective Michael Reaction of 1,3-Dicarbonyl Compounds to Nitroolefins Catalyzed by a Bifunctional Thiourea", J. Am.Chem.Soc., vol. 127, No. 1, pp. 119-125 (2005).

3. IR SPECTRUM OF (3R)-5-METHYL-3-(2-OXO-2{[(1R)-1-PHENYLETHYL]AMINO}ETHYL)HEXANOIC ACID.
BATCH NO. SECONDARY AMIDE

4. XRD CHROMATOGRAM OF (3R)-5-METHYL-3-(2-OXO-2{[(1R)-1-PHENYLETHYL]AMINO}ETHYL)HEXANOIC ACID.

CHIRAL 3-CARBAMOYLMETHYL-5-METHYL HEXANOIC ACIDS, KEY INTERMEDIATES FOR THE SYNTHESIS OF (S)-PREGABALIN

CROSS-REFERENCE TO RELATED APPLICATIONS

This application is a divisional of U.S. patent application Ser. No. 11/523,865, filed Sep. 19, 2006, claims the benefit of priority to U.S. provisional application Ser. Nos. 60/718,689, filed Sep. 19, 2005; 60/754,392, filed Dec. 27, 2005; 60/763,593, filed Jan. 30, 2006; 60/752,434, filed Dec. 20, 2005; 60/753,220, filed Dec. 21, 2005; 60/763,696, filed Jan. 30, 2006; and 60/839,947, filed Aug. 23, 2006, herein incorporated by reference.

FIELD OF THE INVENTION

The invention encompasses the synthesis of (S)-(+)-3-(aminomethyl)-5-methylhexanoic acid, (S)-Pregabalin, via the intermediate, (3R)-5-methyl-3-(2-oxo-2{[(1R)-1-phenylethyl]amino}ethyl)hexanoic acid.

BACKGROUND OF THE INVENTION (S)-Pregabalin, (S)-(+)-3-(aminomethyl)-5-methylhexanoic acid, a compound having the chemical structure,

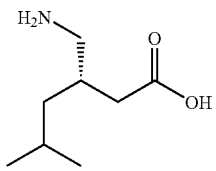

is also known as γ-amino butyric acid or (S)-3-isobutyl GABA. (S)-Pregabalin, marketed under the trade name LYRICA®, has been found to activate GAD (L-glutamic acid decarboxylase). (S)-Pregabalin has a dose dependent protective effect on-seizure, and is a CNS-active compound. (S)-Pregabalin is useful in anticonvulsant therapy, due to its activation of GAD, promoting the production of GABA, one of the brain's major inhibitory neurotransmitters, which is released at 30 percent of the brains synapses. (S)-Pregabalin has analgesic, anticonvulsant, and anxiolytic activity.

Several processes for the synthesis of (S)-Pregabalin are known. For example, see DRUGS OF THE FUTURE, 24 (8), 862-870 (1999). One such process is illustrated in scheme 1.

Scheme 1

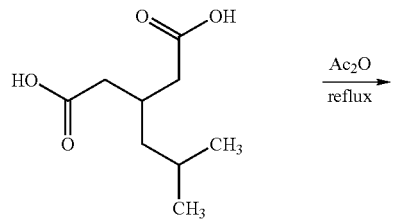

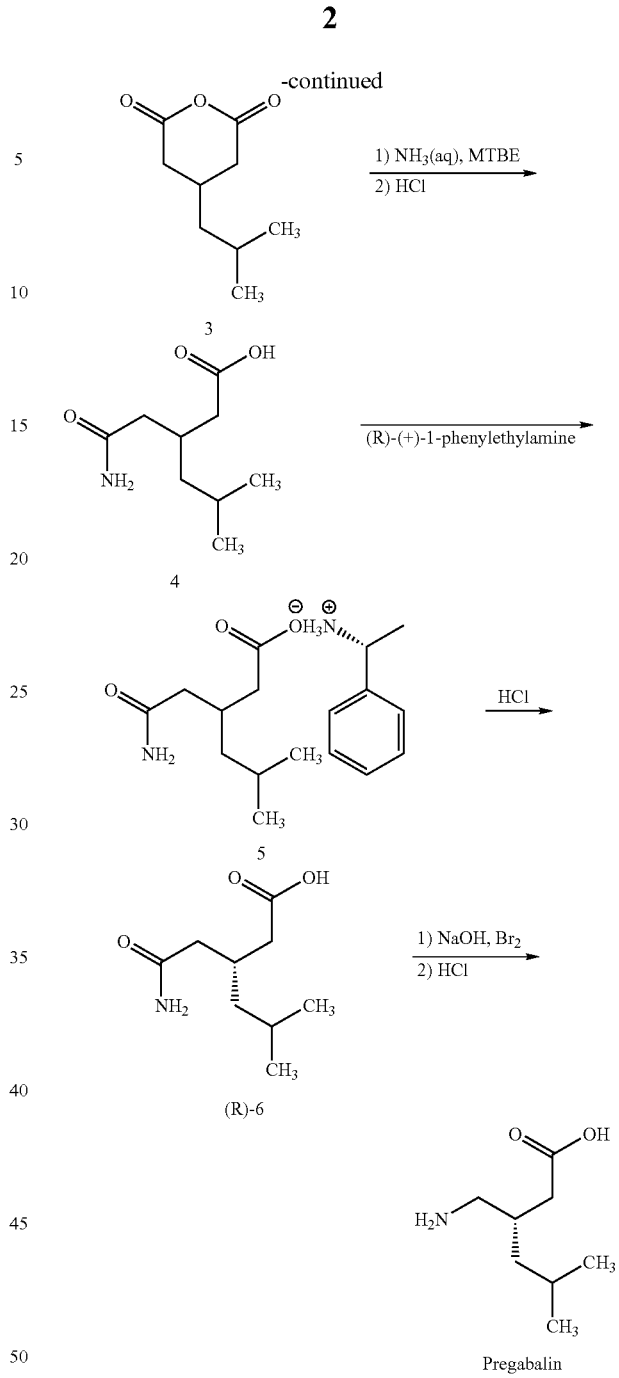

In Scheme 1, 3-isobutyl glutaric acid, compound 2, is converted into the corresponding anhydride, compound 3, by treatment with refluxing acetic anhydride. The reaction of the anhydride with NH₄OH produces the glutaric acid monoamide, compound 4, which is resolved with (R)-1-phenylethylamine, yielding the (R)-phenylethylamine salt of (R)-3-(carbamoylmethyl)-5-methylhexanoic acid, compound 5. Combining the salt with an acid liberates the R enantiomer, compound 6. Finally, a Hoffmann degradation with Br₂/NaOH provides (S)-Pregabalin. A disadvantage of this method is that it requires separating the two enantiomers, thereby resulting in the loss of half the product, such that the process cost is high.

Several stereoselective processes for the synthesis of (S)-Pregabalin have been disclosed. For example, U.S. Pat. No.

5,599,973 discloses the preparation of (S)-Pregabalin using stoichiometric (+)-4-methyl-5-phenyl-2-oxazolidinone as a chiral auxiliary that may be recycled. In general, however, that route is of limited use for scale-up, principally due to the low temperature required for the reactions, the use of pyrophoric reagent, such as, butyl lithium, to side reactions, and due to a low overall yield.

Another process is disclosed in U.S. Patent Application Publication No. 2003/0212290, which discloses asymmetric hydrogenation of a cyano-substituted olefin, compound 7, to produce a cyano precursor of (S)-3-(aminomethyl)-5-methyl hexanoic acid, compound 8, as seen in scheme 2.

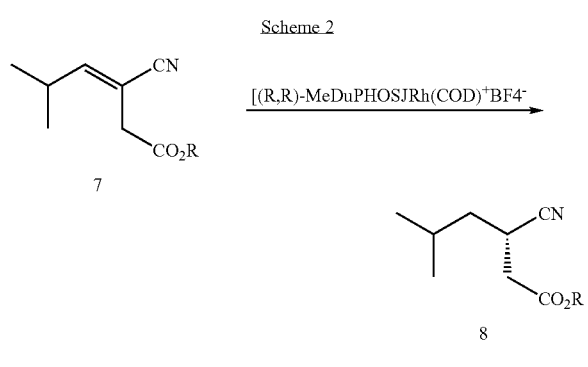

Subsequent reduction of the nitrile in compound 8 by catalytic hydrogenation produces (S)-Pregabalin. The cyano hexenoate starting material, compound 7, is prepared from 2-methyl propanal and acrylonitrile (Yamamoto et al, *Bull. Chem. Soc. Jap.*, 58, 3397 (1985)). However, the disclosed method requires carbon monoxide under high pressure, raising serious problems in adapting this scheme for production scale processes.

A process published by G. M. Sammis, et al., *J. Am. Chem. Soc.*, 125(15), 4442-43 (2003), takes advantage of the asymmetric catalysis of cyanide conjugate addition reactions. The method discloses the application of aluminum salen catalysts to the conjugate addition of hydrogen cyanide to α,β-unsaturated imides as shown in scheme 3. Reportedly, TMSCN is a useful source of cyanide that can be used in the place of HCN. This process is not practicable for large scale production due to the use of highly poisonous reagents. Moreover, the last reductive step requires high pressure hydrogen, which only adds to the difficulties required for adapting this scheme for a production scale process.

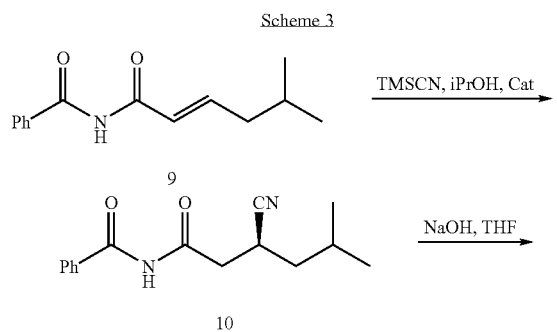

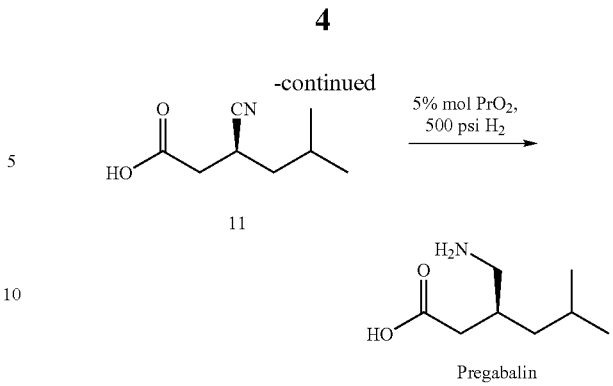

In 1989, Silverman reported a convenient synthesis of 3-alkyl-4-amino acids compounds in SYNTHESIS (1989, 955). Using 2-alkenoic esters as a substrate, a series of GABA analogs were produced by Michael addition of nitromethane to α,β-unsaturated compounds, followed by hydrogenation at atmospheric pressure of the nitro compound to amine moiety as depicted in scheme 4.

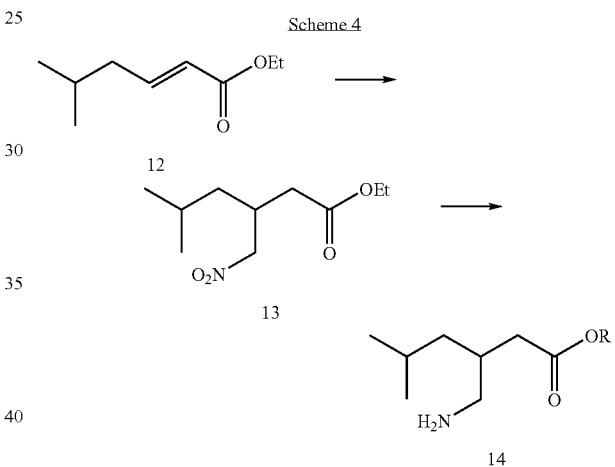

Further resolution of compound 14 may be employed to resolve Pregabalin. This, of course, results in the loss of 50 percent of the product.

Recent studies have indicated that cinchona alkaloids are broadly effective in chiral organic chemistry. A range of nitroalkenes were reportedly treated with dimethyl or diethyl malonate in tetrahydrofuran in the presence of cinchona alkaloids to provide high enantiomeric selectivity of compound 15,

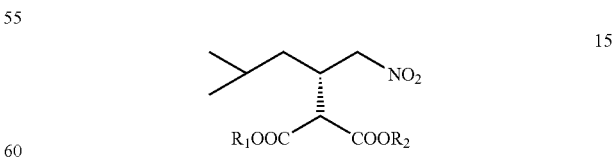

and its analogues. For example, see H. Li, et al., *J. Am. Chem. Soc.*, 126(32), 9906-07 (2004). These catalysts are easily accessible from either quinine or quinidine, and are reportedly highly efficient for a synthetically C—C bond forming asymmetric conjugate addition as shown in scheme 5.

Scheme 5

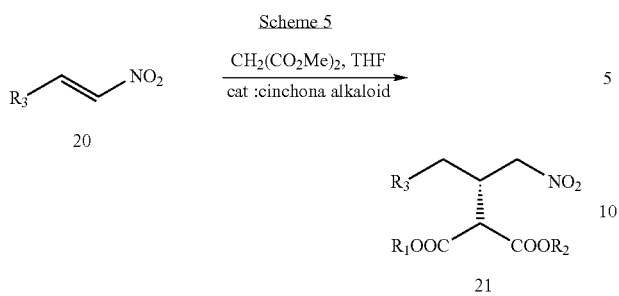

$R_3$ represents several alkyl and aryl groups. The scope of the reaction has been extended to other nitroolefins and applied to prepare ABT-546 employing bis(oxazoline)Mg (OTf)$_2$. See, for example, D. M. Barnes, et al., *J. Am. Chem. Soc.*, 124(44), 13097-13105 (2002).

Other groups have investigated a new class of bifunctional catalysts bearing a thiourea moiety and an amino group on a chiral scaffold. See T. Okino, et al., *J. Am. Chem. Soc.*, 127(1), 119-125 (2005). On the basis of a catalytic Michael addition to the nitroolefin with enantiomeric selectivity, they were able to prepare a series of analogues of compound 15.

Thus, there is a need in the art for new processes for the preparation of (S)-Pregabalin that do not suffer from the disadvantages mentioned above.

SUMMARY OF THE INVENTION

In one embodiment, the invention encompasses a compound of formula 24

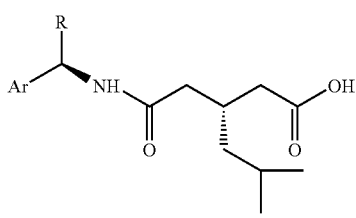

wherein Ar is a $C_{6-10}$ aromatic group selected from the group consisting of naphthyl, phenyl, and substituted phenyl and R is straight or branched $C_{1-4}$ alkyl, ester or carboxylic acid.

Where Ar is phenyl and R is methyl, the compound of formula 24 corresponds to (3R)-5-methyl-3-(2-oxo-2{[(1R)-1-phenylmethyl]amino}ethyl)hexanoic acid of formula 24A.

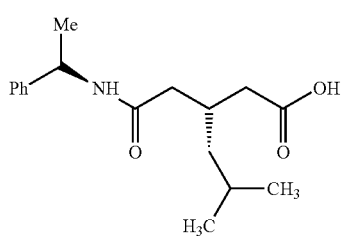

In another embodiment, the invention encompasses the compound of formula 24A in crystalline form.

In another embodiment, the invention encompasses a process for preparing the compound of formula 24 comprising: combining a chiral amine of formula 23,

an organic solvent selected from at least one of aromatic hydrocarbons, ethers, halogenated hydrocarbons, alcohols, esters, alkanes, and ketones, and a base to obtain a mixture; cooling the mixture to a temperature of about 10° C. to about −70° C.; adding to the mixture 3-isobutyl glutaric anhydride of formula 22,

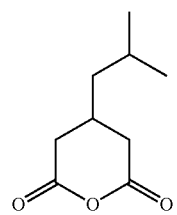

to obtain the compound of formula 24; and recovering the compound of formula 24 from the mixture, wherein Ar is a $C_{6-10}$ aromatic group selected from the group consisting of naphthyl, phenyl, and substituted phenyl and R is straight or branched $C_{1-4}$ alkyl, ester or carboxylic acid.

In another embodiment, the invention encompasses a process for preparing (S)-pregabalin comprising: combining a chiral amine of formula 23,

an organic solvent selected from at least one of aromatic hydrocarbons, ethers, halogenated hydrocarbons, alcohols, esters, alkanes, and ketones, and a base to obtain a mixture; cooling the mixture to a temperature of about 10° C. to about −70° C.; adding to the mixture 3-isobutyl glutaric anhydride of formula 22;

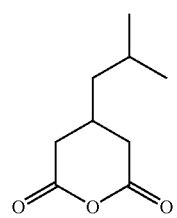

to obtain the compound of formula 24; recovering the compound of formula 24 from the mixture; combining the recovered compound of formula 24, water, an ether, ammonia and an alkali metal, at a temperature of about 10° C. to about –78° C. to obtain a mixture; recovering the compound of formula 25 from the mixture;

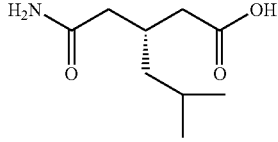

combining the recovered compound of formula 25 with bromine, water, and an alkaline hydroxide to obtain a basic mixture; heating the basic mixture to a temperature of about 60° C. to about 85° C.; adding to the basic mixture a strong mineral acid to obtain an acidic mixture; reacting the acidic mixture with a base to obtain (S)-Pregabalin, and

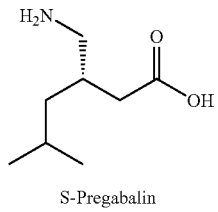

S-Pregabalin recovering (S)-Pregabalin; wherein Ar is a $C_{6-10}$ aromatic group selected from the group consisting of naphthyl, phenyl, and substituted phenyl and R is straight or branched $C_{1-4}$ alkyl, ester or carboxylic acid.

In another embodiment, the invention encompasses a process for preparing (S)-Pregabalin comprising: combining a chiral amine of formula 23,

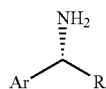

an organic solvent selected from at least one of aromatic hydrocarbons, ethers, halogenated hydrocarbons, alcohols, esters, alkanes, and ketones, and a base to obtain a mixture; cooling the mixture to a temperature of about 10° C. to about –70° C.; adding to the mixture 3-isobutyl glutaric anhydride of formula 22;

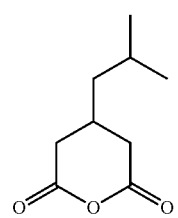

to obtain the compound of formula 24; recovering the compound of formula 24 from the mixture; combining the compound of formula 24 with concentrated sulfuric acid to obtain a mixture; maintaining the mixture at a temperature of about 0° C. to about 50° C., for about 10 hours to about 30 hours; recovering the compound of formula 25 from the mixture;

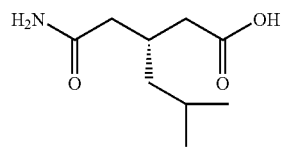

combining the recovered compound of formula 25 with bromine, water, and an alkaline hydroxide to obtain a basic mixture; heating the basic mixture to a temperature of about 60° C. to about 85° C.; adding to the basic mixture a strong mineral acid to obtain an acidic mixture; reacting the acidic mixture with a base to obtain (S)-Pregabalin, and

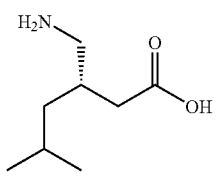

S-Pregabalin recovering (S)-Pregabalin; wherein Ar is a $C_{6-10}$ aromatic group selected from the group consisting of naphthyl, phenyl, and substituted phenyl and R is straight or branched $C_{1-4}$ alkyl, ester or carboxylic acid.

DETAILED DESCRIPTION OF THE INVENTION

The invention provides a stereoselective synthesis of (S)-Pregabalin according to the following scheme:

Scheme 6

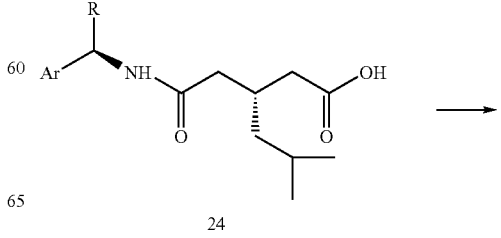

24

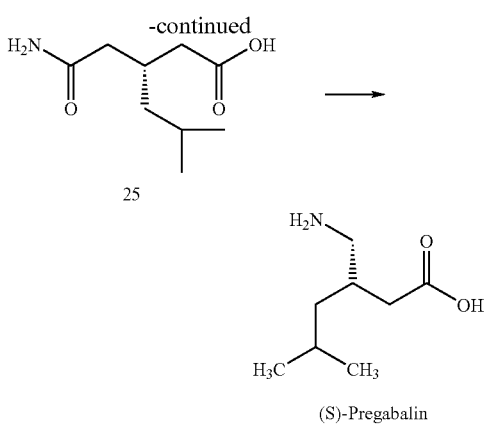

(S)-Pregabalin

The invention encompasses (3R)-5-methyl-3-(2-oxo-2{[(1R)-1-aryl-alkyl]amino}ethyl)hexanoic acids of formula 24,

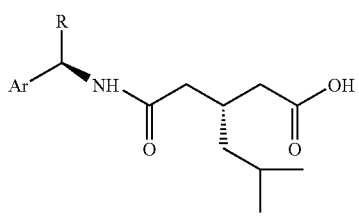

wherein Ar is a $C_{6-10}$ aromatic group selected from the group consisting of naphthyl, phenyl, and substituted phenyl, and R is a straight or branched $C_{1-4}$ alkyl, ester, or carboxylic acid. Preferably, Ar is phenyl. Preferably, R is a straight or branched $C_{1-4}$ alkyl, more preferably, methyl.

Preferably, the substituted phenyl is a phenyl group substituted with at least one of alkoxy, halogen, alkyl, carboxylic acid, or ester. A preferred alkoxy phenyl is methoxyphenyl. Preferred halogenated phenyls are chlorobenzene, bromobenzene, and fluorobenzene. Preferred alkylated phenyls are either toluene or ethylbenzene.

Preferably, the $C_{1-4}$ alkyl is methyl, ethyl, isopropyl, n-butyl, isobutyl or t-butyl. More preferably, the $C_{1-4}$ alkyl is methyl or ethyl, most preferably, methyl.

Preferably, the carboxylic acid substituent is —COOH, —CH$_2$COOH, —CH(CH$_3$)COOH or —C(CH$_3$)$_2$COOH. Preferably the ester is a methylester, ethylester, isopropylester, n-butylester, isobutyl or t-butyl derivative of one of the above-listed carboxylic acid substituents.

When Ar is phenyl and R is methyl, the compound of formula 24 is (3R)-5-methyl-3-(2-oxo-2{[(1R)-1-phenylmethyl]amino}ethyl)hexanoic acid 24A

Figure 1:
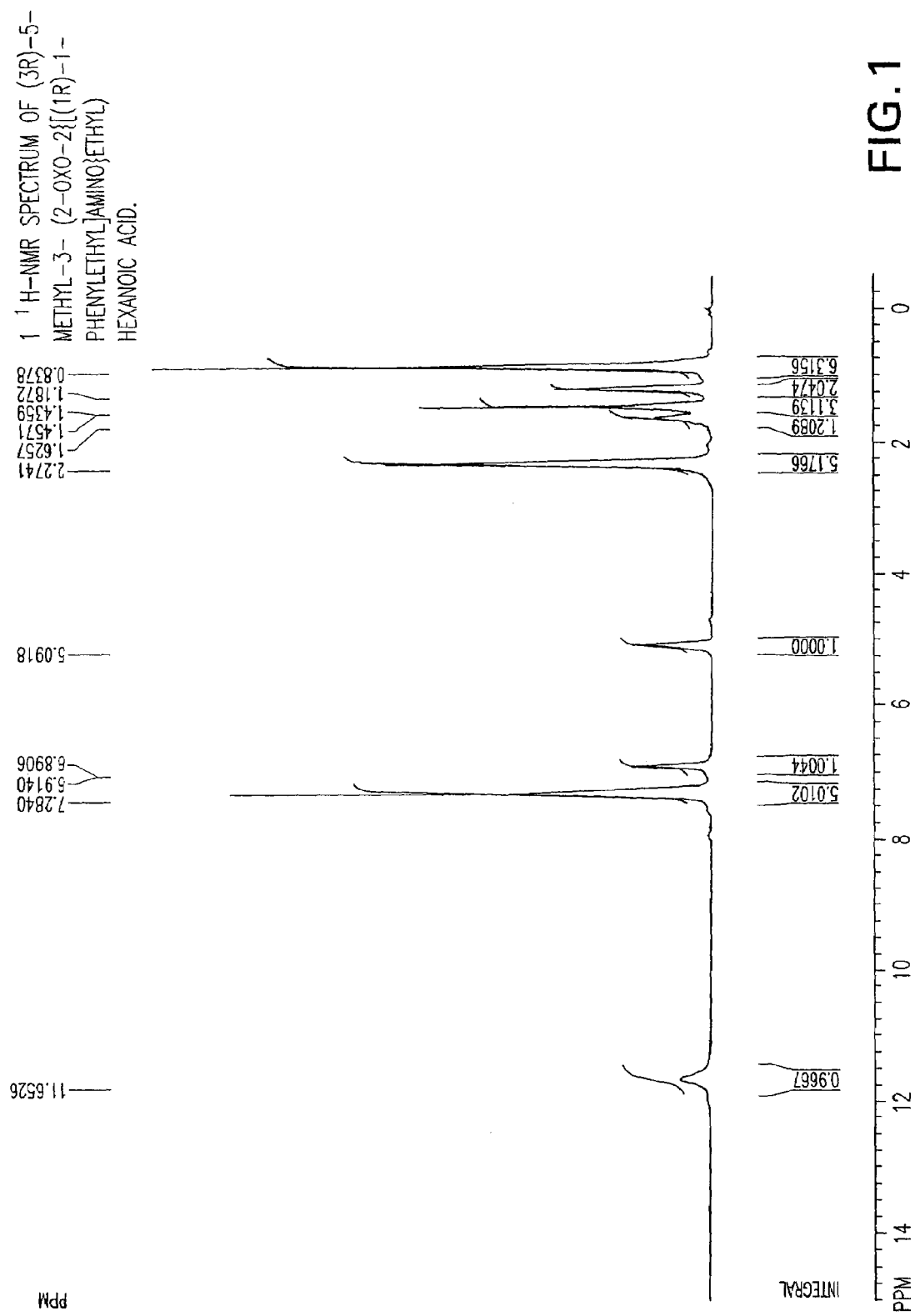
FIG. 1 illustrates an $^1$H-NMR spectrum of (3R)-5-methyl-3-(2-oxo-2{[(1R)-1-phenylethyl]amino}ethyl)hexanoic acid.
Figure 2:
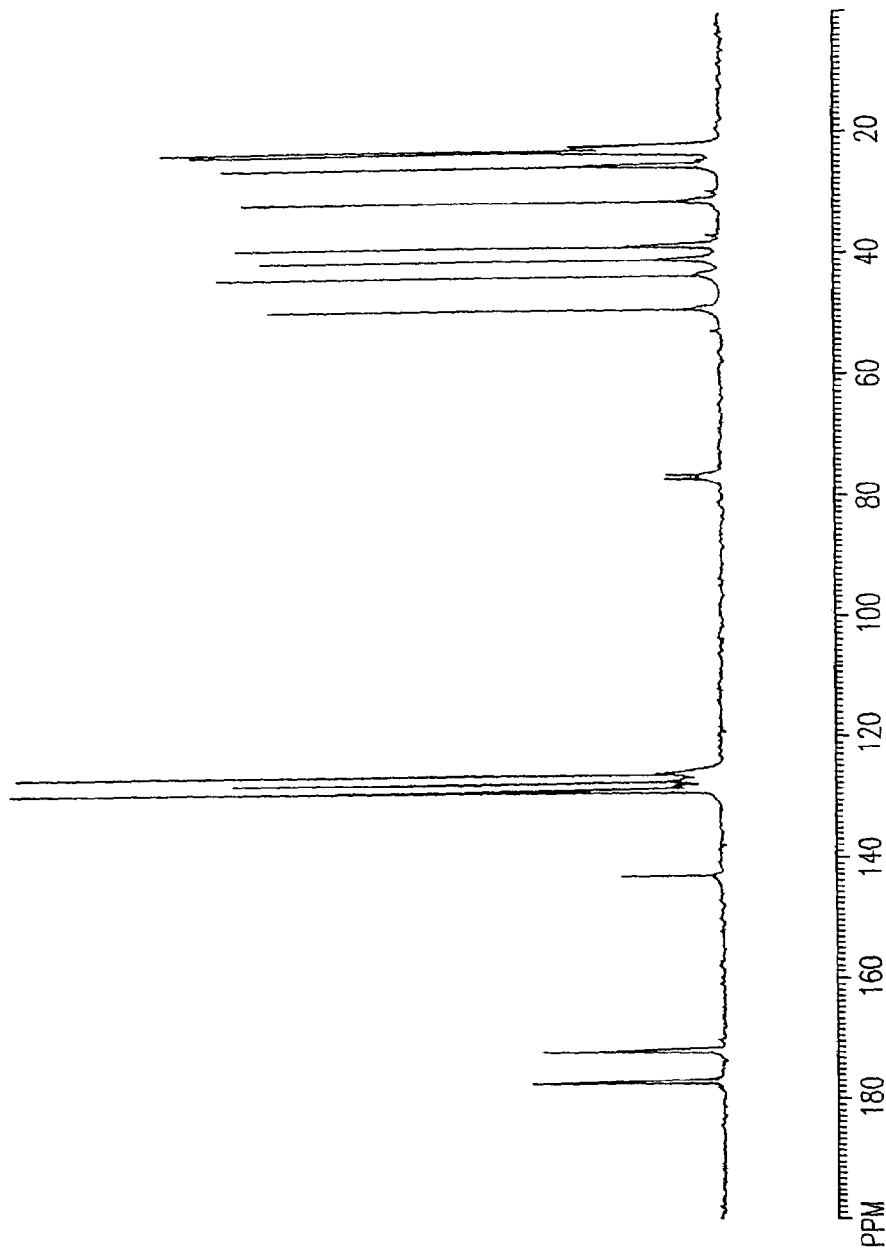
FIG. 2 illustrates a $^{13}$C-NMR spectrum of (3R)-5-methyl-3-(2-oxo-2{[(1R)-1-phenylethyl]amino}ethyl)hexanoic acid.
Figure 3:
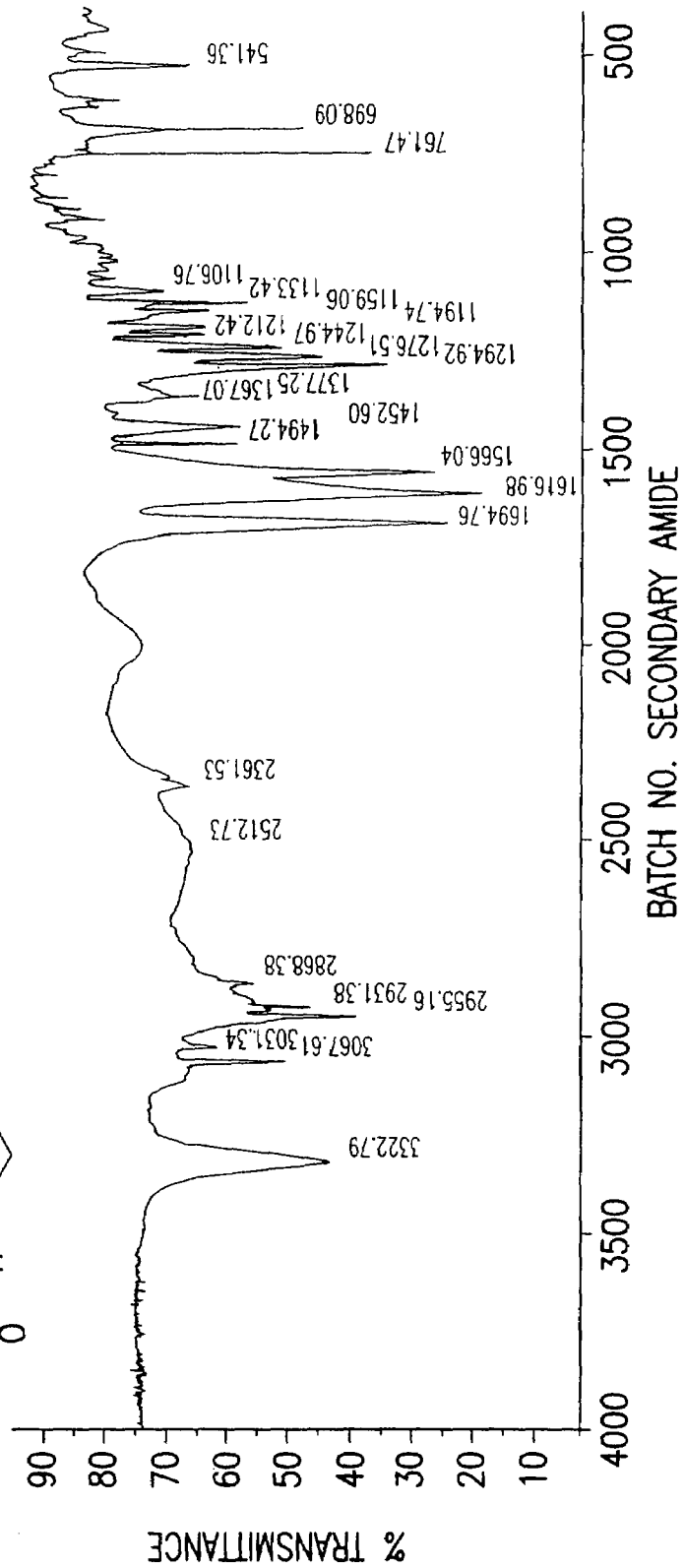
FIG. 3 illustrates an IR spectrum of (3R)-5-methyl-3-(2-oxo-2{[(1R)-1-phenylethyl]amino}ethyl)hexanoic acid.

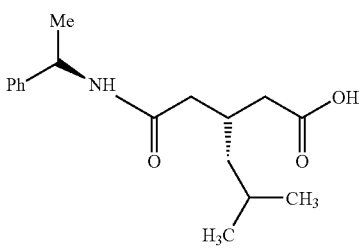

which may be characterized by data selected from a $^{13}$C-NMR spectrum (CDCl$_3$, 75 MHz) having carbon chemical shifts at about 21.74, 22.15, 22.61, 24.12, 24.87, 30.85, 38.1, 40.47, 43.38, 48.88, 126.0, 127.2, 128.49, 143.00, 172.02 and 176.66 ppm; an $^1$H-NMR spectrum (CDCl$_3$, 300 MHz) having hydrogen chemical shifts at about 0.84, 1.19, 1.44-1.46, 1.63, 2.27, 5.09, 6.89-6.91, 7.28 and 11.65 ppm; an IR spectrum having peaks at about 3323, 3318.8, 2955, 1691.98, 1638, 1617, 1566 and 761 cm$^{-1}$. The compound of formula 24A may further be characterized by data selected from a $^{13}$C-NMR spectrum substantially as depicted in FIG. 2; a $^1$H-NMR spectrum substantially as depicted in FIG. 1; and an IR spectrum substantially as depicted in FIG. 3.

Figure 4:
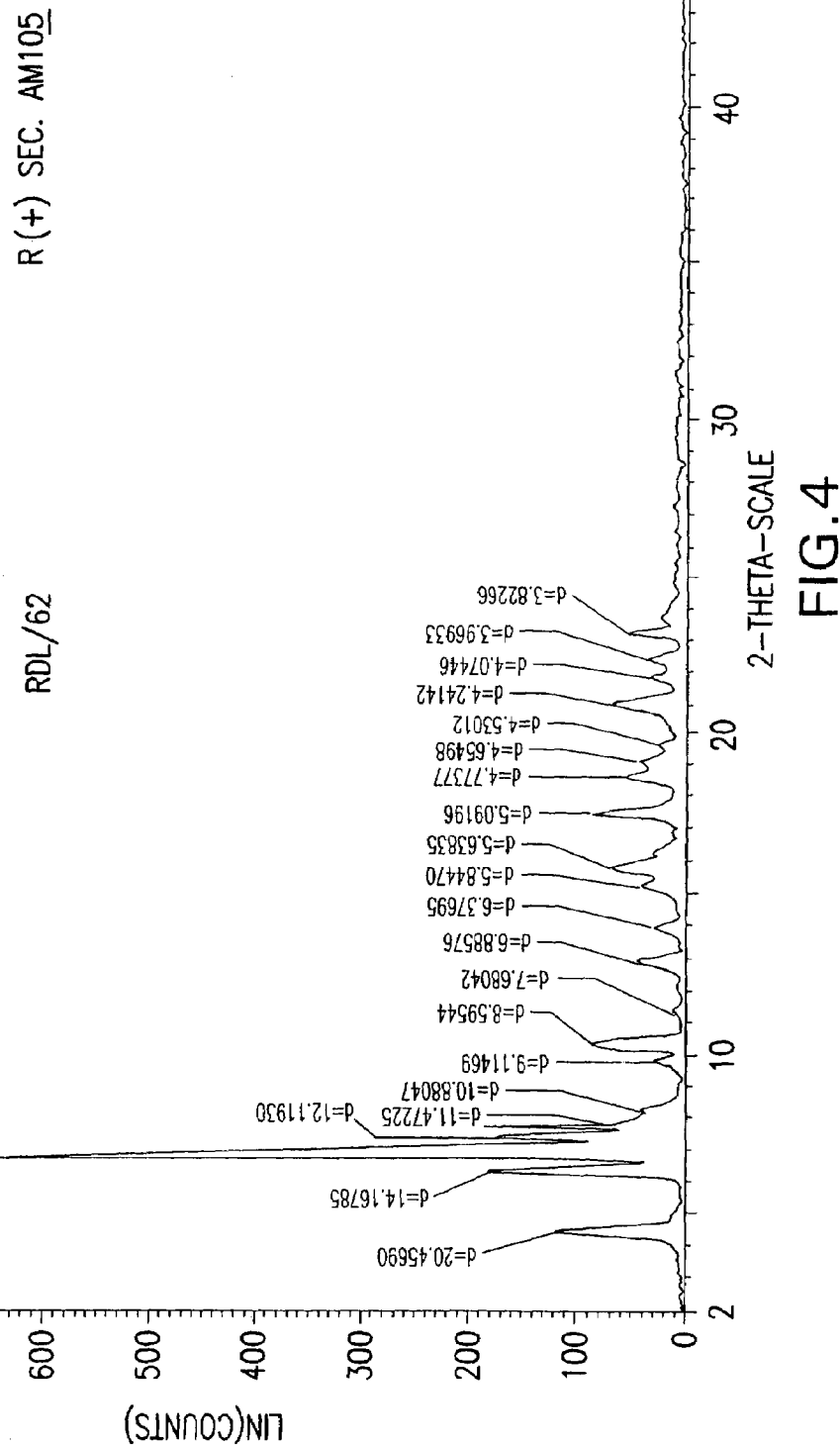
FIG. 4 illustrates a powder X-ray diffraction pattern of (3R)-5-methyl-3-(2-oxo-2{[(1R)-1-phenylethyl]amino}ethyl)hexanoic acid.

The invention also encompasses isolated (3R)-5-methyl-3-(2-oxo-2{[(1R)-1-phenylmethyl]amino}ethyl)hexanoic acid 24A, preferably in a crystalline form. The crystalline form of 24A may be characterized by a powder X-ray diffraction ("PXRD") pattern having peaks at about 4.3°, 6.2° 6.8°, 7.3°, 10.3°, and 17.4° 2θ±0.2° 2θ. The crystalline form of 24A may be further characterized by X-ray powder diffraction peaks at about 7.7°, 8.2°, 9.7°, 11.3°, 12.8°, 13.9°, 15.1°, 15.7°, 18.6°, 19.1°, 19.6°, 20.9°, 21.8°, 22.4°, and 23.3° 2θ±0.2° 2θ. The crystalline form of 24A may be even further characterized by a powder X-ray diffraction pattern substantially as depicted in FIG. 4. Moreover, the crystalline form of 24A may have a melting range of about 95° C. to about 97° C.

The invention also encompasses (3R)-5-methyl-3-(2-oxo-2{[(1R)-1-phenylmethyl]amino}ethyl)hexanoic acid 24A having an optical purity of at least about 80 percent area by HPLC, preferably of at least about 93 percent area by HPLC, more preferably of about 99 percent to about 100 percent area by HPLC.

The compound of formula 24 may be prepared by combining a chiral amine of formula 23,

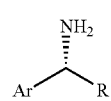

wherein Ar is a $C_{6-10}$ aromatic group selected from the group consisting of naphthyl, phenyl, and substituted phenyl, and R is a straight or branched $C_{1-4}$ alkyl, ester, or carboxylic acid, an organic solvent selected from at least one of aromatic hydrocarbons, ethers, halogenated hydrocarbons, alcohols, esters, alkanes, and ketones, and a base, to obtain a mixture; cooling the mixture to a temperature of about 0° C. to about −70° C.; and adding 3-isobutyl glutaric anhydride of formula 22

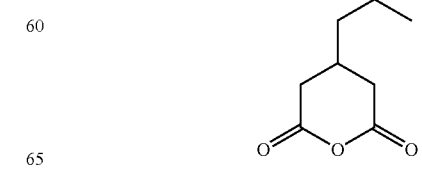

to the mixture to obtain the compound of formula 24,

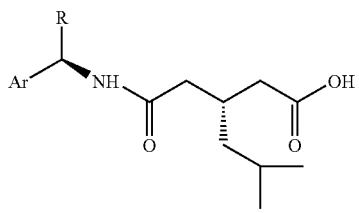

24 which is then recovered from the mixture.

The 3-isobutyl glutaric anhydride of formula 22 may be prepared according to the process disclosed in U.S. Pat. No. 5,616,793.

The chiral amine of formula 23 is commercially available, and is, preferably, a primary amine. Preferably, the primary amine is selected from a group consisting of 1R,2S-ephedrine, naphthyl-α-methyl ethylamine, glycine methylester, methylbenzylamine or a chiral amino acid derivative. Preferably, the primary amine is methylbenzylamine, and more preferably (R)-methylbenzylamine.

Preferably, the aromatic hydrocarbon is a $C_{6-8}$ aromatic hydrocarbon. Preferably, $C_{6-8}$ aromatic aromatic hydrocarbon is toluene, xylene, ethylbenzene, or cumene, more preferably, toluene. Preferably, the ether is a $C_{3-6}$ ether. Preferably, the $C_{3-6}$ ether is tert-butyl methyl ether, tetrahydrofuran, diisopropylether, or diethyl ether, more preferably, tetrahydrofuran. Preferably, the halogenated carbon is a $C_{1-2}$ halogenated hydrocarbon. Preferably, the $C_{1-2}$ halogenated hydrocarbon is dichloroethane, carbon tetrachloride, or chloroform, more preferably, dichloromethane. Preferably, the alcohol is a $C_{1-4}$ alcohol. Preferably, the $C_{1-4}$ alcohol is isopropyl alcohol, ethanol, methanol or n-butanol, more preferably, n-butanol. Preferably, the ester is a $C_{3-6}$ ester. Preferably, the $C_{3-6}$ ester is ethyl acetate, isopropyl acetate, or isobutyl acetate, more preferably, ethyl acetate. Preferably, the alkane is a straight, branched or cyclic $C_{5-7}$ alkane, more preferably, hexane, heptane, or cyclohexane, most preferably, heptane. Preferably, the ketone is a $C_{3-6}$ ketone. Preferably, the $C_{3-6}$ ketone is acetone, methyl isobutyl ketone, or methyl ethyl ketone, most preferably, acetone. The more preferred organic solvent is toluene.

Preferably, the base is an organic base. Preferably, the organic base is a $C_{1-12}$ amine. Preferably, the $C_{1-12}$ amine is selected from the group consisting of diethyl amine, triethyl amine, di-n-propyl amine, di-isopropyl amine, tert-butylamine, tri-n-butylamine, morpholine, piperidine, pyridine, and 4-dimethyl aminopyridine, more preferably, the $C_{1-12}$ amine is 4-dimethyl aminopyridine.

Preferably, the mixture is cooled to a temperature of about 0° C. to about −60° C. before adding the 3-isobutyl glutaric anhydride of formula 22. Preferably, the mixture is maintained at a temperature of about 0° C. to about −60° C. for at least about one hour, more preferably for about one hour to about two hours, before adding the 3-isobutyl glutaric anhydride of formula 22.

The order of combining the reacting substances when preparing the compound of formula 24 may influence the purity and the yield of the final product. Preferably, the chiral amine of formula 23 is combined with the base, prior to the addition of the 3-isobutylglutaric anhydride of formula 22.

The compound of formula 24 may be recovered by any method known to the skilled artisan. Such methods include, but are not limited to, extracting the organic phase with an aqueous basic solution to convert the acidic product to a salt, and acidifying the aqueous phase with a mineral acid to obtain back the acid product.

The compound of formula 24, obtained by the above-described process, has an optical purity of at least about 80 percent area by HPLC, preferably of at least about 93 percent area by HPLC, more preferably of about 99 percent to 100 percent area by HPLC.

The compound of formula 24 may optionally be further purified by crystallization from an organic solvent selected from at least one of esters, nitriles, ethers, $C_{4-6}$ straight, branched, or cyclic hydrocarbons, and $C_{6-10}$ aromatic hydrocarbons. Preferably, the ester is a $C_{3-6}$ ester. Preferably, the $C_{3-6}$ ester is ethyl acetate or isopropyl acetate. Preferably, the nitrile is a $C_2$ nitrile. Preferably, the $C_2$ nitrile is acetonitrile. Preferably, the ether is a $C_{3-6}$ ether. Preferably, the $C_{3-6}$ ether is methyl t-butyl ether. Preferably, the $C_{6-10}$ aromatic hydrocarbon is a $C_{7-9}$ aromatic hydrocarbon. Preferably, the $C_{7-9}$ aromatic hydrocarbon is toluene or xylene. Preferably, the $C_{4-6}$ straight, branched or cyclic hydrocarbon is cyclohexane or hexane, more preferably, cyclohexane. Preferred mixtures are that of xylene and ethyl acetate, hexane and ethyl acetate, cyclohexane and ethyl acetate and toluene and ethyl acetate. The most preferred mixture is that of toluene and ethyl acetate. Most preferably, the solvent is toluene.

The invention further encompasses a process for preparing (S)-Pregabalin by the following scheme:

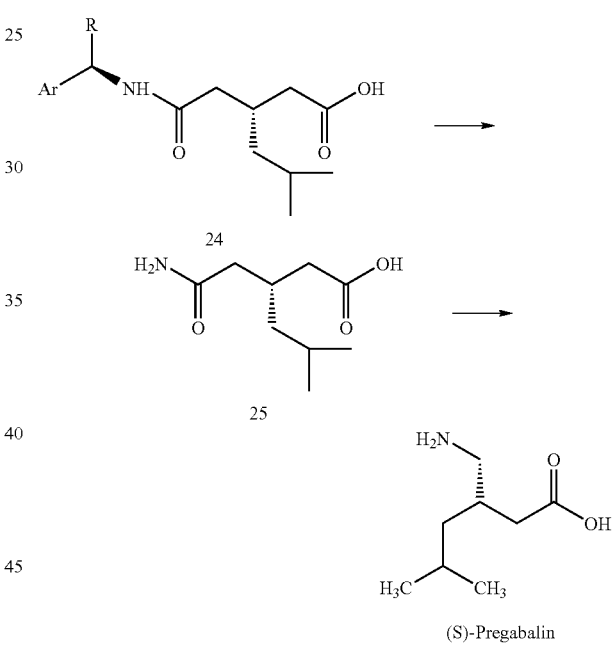

The process comprises preparing a compound of formula 24, converting the compound of formula 24 into a compound of the following formula 25;

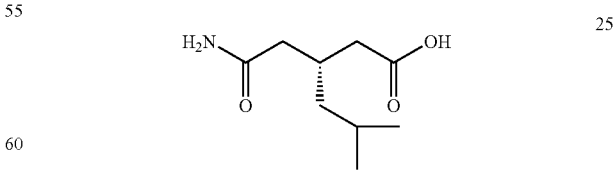

25 converting the compound of formula 25 into (S)-Pregablin; and recovering the (S)-Pregabalin.

Preferably, the compound of formula 24 is prepared by the processes described above.

The compound of formula 24 may be converted into the compound of formula 25 by a process comprising combining the compound of formula 24, water, an ether, ammonia, and an alkali metal at a temperature of about 10° C. to about −78° C. to obtain a mixture; and recovering the compound 25 from the mixture.

Preferably, the compound of formula 24, water, and ether are combined to form a first mixture, to which ammonia and the alkali metal are then added. Preferably, combining the compound of formula 24, water and ether provides a first mixture. Preferably, ammonia and the alkali metal, are then added to the first mixture. Preferably, the compound of formula 24, water, and ether are combined at a temperature of about 10° C. to about −78° C. Preferably, the mixture containing the compound of formula 24, water, and ether is combined with ammonia and an alkali metal at a temperature of about −40° C. to about 5° C.

Preferably, the ether is a $C_{3-6}$ ether. Preferably, the $C_{3-6}$ ether is tetrahydrofuran or dioxane.

Preferably, the ammonia is provided in an aqueous solution, i.e., ammonium hydroxide.

The preferred alkali metal is either lithium or sodium.

Preferably, the reaction mixture is maintained for about 2 to about 10 hours, more preferably for about 6 to about 10 hours.

Alternatively, the compound of formula 24 may converted into the compound of formula 25 by a process comprising combining the compound of formula 24 with concentrated sulfuric acid to obtain a mixture; maintaining the mixture at a temperature of about 0° C. to about 50° C. for about 10 hours to about 30 hours, and recovering the compound of formula 25 from the mixture.

Preferably, the concentrated sulfuric acid contains about 96 percent to about 100 percent volume of sulfuric acid and about 0 percent to about 4 percent volume of water, more preferably, about 100 percent volume of sulfuric acid.

The preferred amount of the concentrated sulfuric acid is about 2 to about 70 mole equivalents, more preferably, about 15 to about 25 mole equivalents, and most preferably, about 15 mole equivalents per mole equivalent of the compound of formula 24.

Preferably, the reaction is maintained at a temperature of about 0° C. to about 50° C., when the amount of the concentrated sulfuric acid is about 2 to about 70 mole equivalents per mole equivalent of the compound of formula 24. More preferably, the reaction is maintained at a temperature of about 25° C. to about 45° C., when the amount of the concentrated sulfuric acid is about 15 to about 25 mole equivalents per mole equivalent of the compound of formula 24, and most preferably, the reaction is maintained at a temperature of about 35° C. to about 40° C., when the amount of the concentrated sulfuric acid is about 15 mole equivalents per mole equivalent of the compound of formula 24.

The compound of formula 25 may be recovered by any method known to the skilled artisan. Such methods include, but are not limited to extraction, followed by drying over anhydrous sodium sulfate.

The compound of formula 25 may optionally be purified by crystallization from a polar organic solvent selected from the group consisting of esters, straight and branched $C_{1-4}$ alcohols, and ethers. Preferably, the ester is a $C_{3-6}$ ester. Preferably, the $C_{3-6}$ ester is ethyl acetate. Preferably, the straight or branched $C_{1-4}$ alcohol is ethanol, methanol, isopropanol, or butanol, more preferably, isopropanol, or n-butanol, and most preferably, n-butanol. Preferably, the ether is a $C_{3-6}$ ether. Preferably, the $C_{3-6}$ ether is tetrahydrofuran or dioxane. The most preferred polar organic solvent is ethyl acetate.

The (R)-3-(carbamoylmethyl)-5-methyl hexanoic acid 25 is obtained by the above crystallization process having an optical purity of at least about 80 percent area by HPLC, preferably of at least about 93 percent area by HPLC, and more preferably of about of about 99 percent to about 100 percent area by HPLC.

The (R)-3-(carbamoylmethyl)-5-methyl hexanoic acid 25 may be converted into (S)-Pregabalin by a process comprising combining the (R)-3-(carbamoylmethyl)-5-methyl hexanoic acid 25 with bromine, water, and an alkali hydroxide to form a basic mixture; heating the basic mixture to a temperature of about 60° C. to about 85° C.; adding a strong mineral acid to the basic mixture to obtain an acidic mixture; adding a base to the acidic mixture; and recovering (S)-Pregabalin.

Preferably, the alkali hydroxide is selected from the group consisting of sodium hydroxide, potassium hydroxide, lithium hydroxide and cesium hydroxide, more preferably, sodium hydroxide.

Preferably, the alkali hydroxide and water are combined, first, to obtain a solution, followed by addition of compound 25 and bromine.

Preferably, compound 25 is added to the solution at a temperature of about 5° C. to about 10° C. After the addition of compound 25, bromine is added, preferably, at a temperature of about 5° C. to about 10° C.

Preferably, a $C_{4-8}$ alcohol is added to the basic mixture prior to the addition of the strong mineral acid. Preferably, the $C_{4-8}$ alcohol is selected from the group consisting of butanol, iso-butanol, 2-butanol, pentanol and iso-pentanol, more preferably, iso-butanol.

Preferably, the strong mineral acid is selected from a group consisting of $H_2SO_4$, HCl, HBr and $H_3PO_4$, more preferably, HCl. Preferably, the addition of the strong mineral acid provides a two-phase system, comprising an organic phase and an aqueous phase.

Preferably, the base is added to the organic phase. The base may be an organic base. The preferred organic base is a secondary or tertiary amine. Preferably, the secondary amine is diisopropylamine or dipropylamine, more preferably, diisopropylamine. Preferably, the tertiary amine is tributyl amine or triethyl amine, more preferably, tributyl amine.

The base may be an inorganic base. Preferably, the inorganic base is an alkali hydroxide or an alkali carbonate. Preferred alkali hydroxides include, but are not limited to, sodium hydroxide, potassium hydroxide, lithium hydroxide, and cesium hydroxide. More preferably, the alkali hydroxide is sodium hydroxide. Preferred alkali carbonates include, but are not limited to, sodium carbonate, sodium bicarbonate, and potassium carbonate. More preferably, the alkali carbonate is sodium carbonate. The more preferred inorganic base is alkali carbonate, most preferably, sodium carbonate.

The addition of the base induces the precipitation of S-Pregabalin. The precipitate of S-Pregabalin may be recovered by any method known to the skilled artisan. Such methods include, but are not limited to, filtering the precipitate, followed by drying.

(S)-Pregabalin is obtained by the above process having an optical purity of about 93 percent to about 100 percent area by HPLC, preferably of about 99 percent to about 100 percent area by HPLC.

Further, 3-isobutyl glutaric anhydride 22 can be regenerated by a process comprising combining the filtrate obtained from the recovery of (S)-Pregabalin with an acid, to obtain a first mixture; heating the first mixture to obtain 3-isobutyl glutaric acid of the following formula;

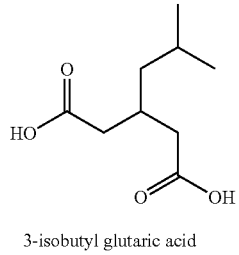

3-isobutyl glutaric acid combining the 3-isobutylglutaric acid with acetic anhydride to obtain a second mixture; heating the second mixture to obtain 3-isobutyl glutaric anhydride 22; and recovering the 3-isobutyl glutaric anhydride 22.

Preferably, the acid is a strong mineral acid, more preferably either 6N to 12N hydrochloric acid or 20 percent to 80 percent sulfuric acid.

Preferably, the first mixture is heated at a temperature of about 100° C. to about 125° C. Preferably, when the mineral acid is hydrochloric acid, the first mixture is maintained at temperature of about 100° C. to about 105° C. Preferably, when the mineral acid is sulfuric acid, the first mixture is maintained at a temperature of about 120° C. to about 125° C.

Preferably, the second mixture of 3-isobutylglutaric acid and acetic anhydride is heated at a temperature of about 135° C. to about 155° C., more preferably at a temperature about 135° C. to about 145° C.

3-isobutyl glutaric anhydride of formula 22 may be recovered by any method known to the skilled artisan. Such methods include, but are not limited to, distilling the excess of acetic anhydride and cooling.

The following non-limiting examples are merely illustrative of the preferred embodiments of the present invention, and are not to be construed as limiting the invention, the scope of which is defined by the appended claims.

EXAMPLES

| Chiral HPLC analysis | |
|---|---|
| Instrument: | Waters-2487 |
| Column: | CHIRAL PACK AD-H, 250 × 4.6 mm, 5 μm |
| Mobile phase: | 2% TFA in n-Hexane/Ethanol-95/5 |
| Flow: | 0.5 ml/minute |
| Temperature: | 30° C. |
| Wavelength: | 210 nm/UV visible spectrophotometer |

| $^1$H-NMR analysis | | | |
|---|---|---|---|
| F2-Acquisition parameters | | F2-Processing parameters | |
| Instrument | dpx 300 | SI | 32768 |
| Probhd | 5 mm Dual Z5 | SF | 300.1300069 MHz |
| Pulprog | zg | WDW | EM |
| TD | 16384 | SSB | 0 |
| Solvent | CDCl$_3$ | LB | 0.01 Hz |
| NS | 8 | GB | 0 |
| DS | 0 | PC | 1.4 |
| SWH | 8992.806 Hz | | |
| FIDRES | 0.548877 Hz | | |
| AQ | 0.9110004 sec | | |
| RG | 16 | | |
| DW | 55.600 μsec | | |
| DE | 4.50 μsec | | |
| TE | 300.0 K | | |
| D1 | 5 seconds | | |
| P1 | 11.35 μsec | | |
| SFO1 | 300.1342018 MHz | | |
| NUC1 | 1H | | |
| PL1 | 0 dB | | |

| $^{13}$C-NMR analysis | | | |
|---|---|---|---|
| F2-Acquisition parameters | | F2-Processing parameters | |
| Instrument | dpx 300 | SI | 16384 |
| Probhd | 5 mm Dual Z5 | SF | 75.4677595 MHz |
| Pulprog | zgdc | WDW | EM |
| TD | 16384 | SSB | 0 |
| Solvent | CDCl$_3$ | LB | 10.00 Hz |
| NS | 4959 | GB | 0 |
| DS | 0 | PC | 1.4 |
| SWH | 18832.393 Hz | | |
| FIDRES | 1.149438 Hz | | |
| AQ | 0.4350452 sec | | |
| RG | 9195.2 | | |
| DW | 26.550 μsec | | |
| DE | 4.50 μsec | | |
| TE | 300.0 K | | |
| D11 | 0.03 second | | |
| PL12 | 17.8Db | | |
| Cpdprg2 | waltz 16 | | |
| PCPD2 | 90.00 μsec | | |
| SFO2 | 300.1330013 MHz | | |
| NUC2 | 1H | | |
| PL2 | 0 dB | | |
| D1 | 1 second | | |
| P1 | 9.4 μsec | | |
| DE | 4.5 μsec | | |
| SFO1 | 75.4767751 MHz | | |
| NUC1 | 13C | | |
| PL1 | 0 dB | | |

| IR analysis KBr pellets | |
|---|---|
| Number of sample scans | 16 |
| Number of background scans | 16 |
| Scanning parameters | 4000-500 cm$^{-1}$ |
| Resolution | 4 |
| Sample gain | 8 |
| Mirror velocity | 0.6329 |
| Aperture | 100 |

| X-ray analysis | |
|---|---|
| Instrument | SIEMENS "Model: D-5000 |
| Copper radiation | 1.5406 A |

-continued

X-ray analysis

| Scanning parameters | 2-50° 2θ. |
|---|---|
| Step scan | 0.03° |
| Step time | 0.5 second |

Example 1

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with toluene (400 ml), (R)-(+)-phenylethylamine (38.59 g, 0.0.319 mole) and 4-dimethylaminopyridine (0.358 g, 0.0029 mole). The mixture was cooled to a temperature of −50° C. to −60° C., followed by addition of a solution of 3-isobutyl glutaric anhydride (50 g, 0.294 mole) in toluene (100 ml), over a period of 45-60 minutes, and stirring for additional 1.5-2 hours, at a temperature of −50° C. to −60° C. The mixture was then extracted with 3.5-4.0 percent aqueous solution of NaOH (1000 ml), and the aqueous phase was washed with toluene (1×250 ml). The pH of the aqueous phase was adjusted to 2-2.5 by adding a solution hydrochloric acid (1-12N). The aqueous phase was further extracted with ethyl acetate (1×300 ml and 1×100 ml), followed by drying the combined ethyl acetates extracts over anhydrous sodium sulfate, and stripping off the solvents to obtain a residue. The residue was crystallized from ethyl acetate and toluene mixture to get 66 g (77.2 percent yield) of a white solid of (3R)-5-methyl-3-(2-oxo-2-{[(1R)-1-phenylethyl]amino}ethyl)hexanoic acid with an optical purity of 99.91 percent, as measured by chiral HPLC.

Example 2

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and mechanical stirrer, was charged with ethyl acetate (100 ml), (R)-(+)-phenylethylamine (26.69 g, 0.0.22 mole) and 4-dimethylaminopyridine (2.69 g, 0.15.mole): The mixture was cooled to a temperature of −50° to −60° C., followed by addition of a solution of 3-isobutyl glutaric anhydride (25 g, 0.147 mole) in ethyl acetate (50 ml), over a period of 25-30 minutes, and stirring for additional 1.5-2 hours, at a temperature of −50 to −60° C. The mixture was then extracted with 5-4 percent aqueous solution of NaOH (500 ml), and the aqueous phase was separated. The pH of the aqueous phase was adjusted to 2-2.5 by adding a solution hydrochloric acid (1-12N). The aqueous phase was further extracted with ethyl acetate (1×150 ml and 1×100 ml), followed by drying the combined ethyl acetates extracts over anhydrous sodium sulfate, and stripping off the solvent to obtain a residue. The residue was crystallized from ethyl acetate and toluene mixture to get 35.43 g (82.87 percent yield) of a white solid of (3R)-5-methyl-3-(2-oxo-2-{[(1R)-1-phenylethyl]amino}ethyl)hexanoic acid with an optical purity of 99.4 percent, as measured by chiral HPLC.

Example 3

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with toluene (100 ml), (R)-(+)-phenylethylamine (35.58 g, 0.294 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in toluene (25 ml), over a period of 15-20 minutes, and stirring for additional 1.5-2 hours, at a temperature of 0°-5° C. The mixture was then extracted with 2.5-3.0 percent aqueous solution of NaHCO$_3$ solution (500 ml), and the aqueous phase was washed with toluene (1×100 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 28.4 g (66.4 percent yield) of a white solid of (3R)-5-methyl-3-(2-oxo-2-{[(1R)-1-phenylethyl]amino}ethyl)hexanoic acid with an optical purity of 99.6 percent, as measured by chiral HPLC.

Example 4

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer), was charged with tert-butyl methyl ether (100 ml), (R)-(+)-phenylethylamine (43.05 g, 0.355 mole) and 4-dimethylaminopyridine (0.258 g, 0.0021 mole). The mixture was cooled to a temperature of 0-5° C., followed by addition of a solution of 3-isobutyl glutaric anhydride (40 g, 0.235 mole) in tert-butyl methyl ether (100 ml), over a period of 15-20 minutes, and stirring for additional 1.5-2 hours, at a temperature of 0-5° C. The mixture was then extracted with 5 percent aqueous solution of NaHCO$_3$ solution (700 ml), and the aqueous phase was washed with tert-butyl methyl ether (1×100 ml). The pH of the aqueous phase was adjusted to 2-2.5 by adding a 1-12N solution of hydrochloric acid. The aqueous phase was further extracted with ethyl acetate (1×200 ml), followed by drying the combined ethyl acetates extracts over anhydrous sodium sulfate, and stripping off the solvents, to obtain a residue. The residue was crystallized from ethyl acetate and toluene mixture to get 44.5 g (70 percent yield) of a white solid of (3R)-5-methyl-3-(2-oxo-2-{[(1R)-1-phenylethyl]amino}ethyl)hexanoic acid with an optical purity of 99.19 percent, as measured by chiral HPLC.

Example 5

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with methylene chloride (100 ml), (R)-(+)-phenylethylamine (53.38 g, 0.44 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in methylene chloride (25 ml), over a period of 15-20 minutes, and stirring for additional 1.5-2 hours, at a temperature of 0-5° C. The mixture was then extracted with 2.5-3 percent aqueous solution of NaHCO$_3$ solution (500 ml), and diluted with water (1000 ml) followed by washing the aqueous phase with toluene (1×100 ml and 1×50 ml). The pH of the aqueous phase was adjusted to 2-2.5 by adding a 1-12N solution Of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 26.2 g (61.3 percent yield) of a white solid of (3R)-5-methyl-3-(2-oxo-2-{[(1R)-1-phenylethyl]amino}ethyl)hexanoic acid with an optical purity of 99.41 percent, as measured by chiral HPLC.

Example 6

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with IPA (100 ml), (R)-(+)-phenylethylamine (35.58 g, 0.147 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in IPA (25 ml), over a period of 15-20 minutes, and stirring for additional 1.5-2 hours, at a temperature of 0-5° C. The solvent was stripped off and the residue was extracted with 2.5-3 percent aqueous solution of NaHCO$_3$ solution (500 ml), and diluted with water (1000 ml) followed by washing the aqueous phase with toluene (1×100 ml and 1×50 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 25.2 g (58.9 percent yield) of a white solid of (3R)-5-methyl-3-(2-oxo-2-{[(1R)-1-phenylethyl]amino}ethyl)hexanoic acid with an optical purity of 99.34 percent, as measured by chiral HPLC.

Example 7

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with ethyl acetate (100 ml), (R)-(+)-phenylethylamine (35.58 g, 0.147 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in ethyl acetate (25 ml), over a period of 15-20 minutes, and stirring for additional 1.5-2 hours, at a temperature of 0-5° C. The solvent was stripped off and the residue was extracted with 2.5-3 percent aqueous solution of NaHCO$_3$ solution (500 ml), and diluted with water (1000 ml) followed by washing the aqueous phase with toluene (1×100 ml and 1×50 ml). The pH of the aqueous phase was adjusted to 2-2.5 by adding a 1-12 N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 26.6 g (61.5 percent yield) of a white solid of (3R)-5-methyl-3-(2-oxo-2-{[(1R)-1-phenylethyl]amino}ethyl)hexanoic acid with an optical purity of 99.3 percent, as measured by chiral HPLC.

Example 8

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with acetone (100 ml), (R)-(+)-phenylethylamine (35.58 g, 0.147 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in acetone (25 ml), over a period of 15-20 minutes, and stirring for additional 1.5-2 hours, at a temperature of 0-5° C. The solvent was stripped off and the residue was extracted with 2.5-3 percent aqueous solution of NaHCO$_3$ solution (500 ml), and diluted with water (1000 ml) followed by washing the aqueous phase with toluene (1×100 ml and 1×50 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 24 g (56 percent yield) of a white solid of (3R)-5-methyl-3-(2-oxo-2-{[(1R)-1-phenylethyl]amino}ethyl)hexanoic acid with an optical purity of 99.32 percent, as measured by chiral HPLC.

Example 9

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with hexane (100 ml), (R)-(+)-phenylethylamine (35.58 g, 0.147mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in hexane (25 ml), over a period of 15-20 minutes, and stirring for additional 1.5-2 hours, at a temperature of 0-5° C. The mixture was then extracted with 2.5-3 percent aqueous solution of NaHCO$_3$ solution (500 ml), and diluted with water (1000 ml) followed by washing the aqueous phase with toluene (1×100 ml and 1×50 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 22.2 g (51.9 percent yield) of a white solid of (3R)-5-methyl-3-(2-oxo-2-{[(1R)-1-phenylethyl]amino}ethyl)hexanoic acid with an optical purity of 99.27 percent, as measured by chiral HPLC.

Example 10

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with a mixture of cyclohexane and toluene (100 ml) in a ratio of 1 to 1, (R)-(+)-phenylethylamine (35.58 g, 0.147 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in mixture of cyclohexane and toluene (100 ml) in a ratio of 1 to 1, (25 ml), over a period of 15-20 minutes, and stirring for additional 1.5-2 hours, at a temperature of 0-5° C. The mixture was then extracted with 2.5-3 percent aqueous solution of NaOH solution (500 ml), and the aqueous phase was washed with toluene (1×50 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 28.7 g (67 percent yield) of a white solid of (3R)-5-methyl-3-(2-oxo-2-{[(1R)-1-phenylethyl]amino}ethyl)hexanoic acid with an optical purity of 99.34 percent, as measured by chiral HPLC.

Example 11

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with methyl isobutyl ketone (100 ml), (R)-(+)-phenylethylamine (35.58 g, 0.147 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in methyl isobutyl ketone (25 ml), over a period of 15-20 minutes, and stirring for additional 1.5-2 hours, at a temperature of 0-5° C. The solvent was stripped off and the residue was extracted with 2.5-3 percent aqueous solution of NaHCO$_3$ solution (500 ml), followed by washing the aqueous phase with toluene (1×100 ml and 1×50 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 25.2 g (58.9 percent yield) of a white solid of (3R)-5-methyl-3-(2-oxo-2-{[(1R)-1-phenylethyl] amino}ethyl)hexanoic acid with an optical purity of 99.3 percent, as measured by chiral HPLC.

Example 12

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with toluene (100 ml), (R)-(+)-phenylethylamine (35.58 g, 0.147 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in toluene (25 ml), over a period of 15-20 minutes, and stirring for additional 1.5-2 hours, at a temperature of 0-5° C. The mixture was then extracted with 2.5-3 percent aqueous solution of NaOH solution (500 ml), and the aqueous phase was washed with toluene (1×50 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 29.3 g (68.5 percent yield) of a white solid of (3R)-5-methyl-3-(2-oxo-2-{[(1R)-1-phenylethyl]amino}ethyl)hexanoic acid with an optical purity of 99.34 percent, as measured by chiral HPLC.

Example 13

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with methanol (100 ml), (R)-(+)-phenylethylamine (35.58 g, 0.147 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in methanol (25 ml), over a period of 15-20 minutes, and stirring for additional 1.5-2 hours, at a temperature of 0-5° C. The solvent was stripped off and the residue was extracted with 2.5-3 percent aqueous solution of NaHCO$_3$ solution (500 ml), and diluted with water (1000 ml) followed by washing the aqueous phase with toluene (1×100 ml and 1×50 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 22.2 g (51.76 percent yield) of a white solid of (3R)-5-methyl-3-(2-oxo-2-{[(1R)-1-phenylethyl] amino}ethyl)hexanoic acid with an optical purity of 99.1 percent, as measured by chiral HPLC.

Example 14

Preparation of (3R)-5-methyl-3-(2-oxo-2{[(1R)-1-phenylethyl]amino}ethyl)hexanoic acid compound (24)

A three-necked flask equipped with an addition funnel, thermometer pocket, drying tube and a mechanical stirrer, was charged with ethanol (100 ml), (R)-(+)-phenylethylamine (35.58 g, 0.147 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in ethanol (25 ml), over a period of 15-20 minutes, and stirring for additional 1.5-2 hours, at a temperature of 0-5° C. The solvent was stripped off and the residue was extracted with 2.5-3 percent aqueous solution of NaOH solution (500 ml), and diluted with water (1000 ml) followed by washing the aqueous phase with toluene (1×100 ml and 1×50 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 22.7 g (53.09 percent yield) of a white solid of (3R)-5-methyl-3-(2-oxo-2-{[(1R)-1-phenylethyl] amino}ethyl)hexanoic acid with an optical purity of 99.17 percent, as measured by chiral HPLC.

Example 15

Preparation of (3R)-5-methyl-3-(2-oxo-2{[(1R)-1-phenylethyl]amino}ethyl)hexanoic acid compound (24)

A three-neck-flask equipped with an addition funnel, thermometer pocket, drying tube and a mechanical stirrer, was charged with n-butanol (100 ml), (R)-(+)-phenylethylamine (35.58 g, 0.147 mole) and 4-dimethylaminopyridine (0.18 g, 0.00147 mole). The mixture was cooled to a temperature of 0-5° C., followed by addition of a solution of 3-isobutyl glutaric anhydride (25 g, 0.147 mole) in n-butanol (25 ml), over a period of 15-20 minutes, and stirring for additional 1.5-2 hours, at a temperature of 0-5° C. The solvent was stripped off and the residue was extracted with 2.5-3 percent aqueous solution of NaOH solution (500 ml), and diluted with water (1000 ml) followed by washing the aqueous phase with toluene (1×100 ml and 1×50 ml). The pH of the aqueous phase was adjusted to 2-2.5 by adding a 1-12N solution of hydrochloric acid. The aqueous phase was further extracted with ethyl acetate (1×150 ml and 1×50 ml), followed by drying the combined ethyl acetates extracts over anhydrous sodium sulfate, and stripping off the solvents, to obtain a residue. The residue was crystallized from ethyl acetate and toluene mixture to get 23.1 g (54.03 percent yield) of a white solid of (3R)-5-methyl-3-(2-oxo-2-{[(1R)-1-phenylethyl] amino}ethyl)hexanoic acid with an optical purity of 99.16 percent, as measured by chiral HPLC.

Example 16

Preparation of (R)-3-carbamoylmethyl-5methyl hexanoic acid compound (25)

A 2 liter four-necked flask, equipped with a mechanical stirrer, thermometer pocket and a liquid ammonia inlet, was charged with 24 (7.5 g, 0.0257 mole) from examples 1-13, tetrahydrofuran (112.5 ml) and water (7.5 ml). The reaction mixture was cooled to −40° C. and liquid ammonia (700 ml) was added followed by addition of small pieces of sodium metal (2.5 g). The resultant reaction mixture was stirred vigorously for 6-10 hours until the ammonia had evaporated. Water (100 ml) was added to the reaction mass under $N_2$ atmosphere at 5-10° C., followed by separating the phases. The pH of the aqueous phase was adjusted to 1.5-1.7 using hydrochloric acid, followed by extractions with methylene dichloride (2×250 ml). The combined methylene dichloride layers were dried over anhydrous sodium sulfate and the solvent was stripped off. The residue was crystallized from ethyl acetate to get 1.89 g (39.37 percent yield) of (R)-3-carbamoylmethyl-5-methylhexanoic acid with optical purity of 99.81 percent as measured by chiral HPLC.

Compound 25 is characterized by: 1. IR (KBr):3436.17, 1712.53, 1644.29 cm$^{-1}$. 2. $^1$H NMR (CDCl$_3$): δ 0.89-0.90 (d, 6H), 1.24-1.26 (t, 2H), 1.63-1.72 (septet, 1H), 2.04-2.11 (d, 2H), 2.26-2.32 (d, 2H), 6.50 (s, 1H), 6.94 (s,1H). 3. $^{13}$C NMR (CDCl$_3$): δ 21.79, 22.02, 22.61, 24.27, 29.62, 37.86, 38.82, 39.48, 42.71, 174.39, 174.83.

Example 17

Preparation of (R)-3-carbamoylmethyl-5methyl hexanoic acid compound (25)

A 2 liter four neck-flask, equipped with a mechanical stirrer, thermometer pocket and a liquid ammonia inlet, was charged with 24 (7.0 g, 0.024 mole) from examples 1-13, tetrahydrofuran (70 ml) and water (5 ml). The reaction mixture was cooled to −40° C. and liquid ammonia (400 ml) was added followed by addition of small pieces of lithium metal (0.667 g, 0.0962 mole). The resultant reaction mixture was stirred vigorously for 6-10 hours until the ammonia had evaporated. Water (50 ml) was added to the reaction mass under $N_2$ atmosphere at 5-10° C., followed by separating the phases. The pH of the aqueous phase was adjusted to 1.5-1.7 using hydrochloric acid, followed by extractions with ethyl acetate (1×150 ml and 1×100 ml). The combined ethyl acetate layers were dried over anhydrous sodium sulfate and the solvent was stripped off. The residue was crystallized from ethyl acetate to get 2.66 g (59.37 percent yield) of (R)-3-carbamoylmethyl-5-methylhexanoic acid with optical purity of 99.8 percent as measured by chiral HPLC.

Example 18

Preparation of (R)-3-carbamoylmethyl-5methyl hexanoic acid compound (25)

A 250 ml four-necked flask, equipped with thermometer pocket and drying tube, was charged concentrated sulfuric acid (36.4 g, 0.37 mole) and 24 (2.0 g, 0.0068 mole). The reaction mixture was stirred over night at 25-30° C., and then quenched with crushed ice (150 g) and stirred. The aqueous phase was extracted with ethyl acetate (1×150 ml and 1×150 ml), followed by washing the ethyl acetate layer with water, and finally drying over anhydrous sodium sulfate. The solvent was stripped off, and the product was crystallized from ethyl acetate obtaining 0.5 g (39 percent yield) of (R)-3-carbamoylmethyl-5-methylhexanoic acid with optical purity of 99.5 percent as measured by chiral HPLC.

Example 19

Regeneration of 3-isobutylglutaric acid

A 0.5 liter four necked-flask, equipped with a mechanical stirrer, thermometer pocket, and condenser, was charged with a residue of the secondary amide after crystallization (5 g) from examples 1-13 and concentrated hydrochloric acid (100 ml). The reaction mixture was refluxed at 100-105° C. for 20-24 hours, and then cooled to 20-25° C. The pH of the mixture was adjusted to 10-11 with a 20 percent solution of sodium hydroxide. The aqueous layer was extracted with toluene (2×50 ml) and the pH of the aqueous layer was adjusted to 1.5-2 with concentrated hydrochloric acid, followed by extractions with methylene chloride (2×50 ml). The combined methylene chloride layers were dried over anhydrous sodium sulfate and the solvent was stripped off to obtain 3-isobutyl glutaric acid (3.39 g) in purity of 88.48 percent as measured by GC.

3-isobutylglutaric acid is characterized by: 1. IR (KBr): 1713.27 cm$^{-1}$. 2. $^1$H NMR (CDCl$_3$): δ 0.89-0.92 (d, 6H), 1.25 (t, 2H), 1.6-1.69 (septet, 1H), 2.42 (s, 4H), 11.96 (s,2H). 3. $^{13}$C NMR (CDCl$_3$): δ 22.39, 25.06, 28.11, 29.50, 38.45, 43.38, 179.17.

Example 20

Regeneration of 3-isobutylglutaric acid

A 0.5 liter four-necked flask, equipped with a mechanical stirrer, thermometer pocket and a condenser, was charged with the residue of the secondary amide after crystallization (5 g) from example 1-13, and 70 percent of sulfuric acid (100 ml). The reaction mixture was refluxed at 120-125° C. for 1-2 hours, and then it was cooled to 20-25° C., followed by adjusting the pH to 10-11 with a 20 percent solution of sodium hydroxide solution. The aqueous layer was extracted with toluene (2×50 ml) and the pH of the aqueous layer was adjusted to 1.5-2 with concentrated. Hydrochloric acid, and then it was extracted with methylene chloride 92×50 ml). The combined methylene dichloride layers were dried over anhydrous sodium sulfate and the solvent was stripped off to obtain 3-isobutyl glutaric acid (3.3 g).

Example 21

Converting 3-isobutylglutaric acid to 3-isobutylglutaric anhydride, compound 22

A 1 liter four-necked flask equipped with a mechanical stirrer, thermometer pocket and condenser, was charged with 3-isobutyl glutaric acid (250 g) and acetic anhydride (62.7 g). The reaction mixture was refluxed at 135°-145° C. for 2.5-3 hours, followed by distilling out the unreacted acetic anhydride at 147°-155° C., and then the distillation was continued under vacuum to ensure removal of traces of unreacted acetic anhydride. The residue was cooled to 25°-30° C. to obtain 220-225 g of 3-isobutylglutaric anhydride.

Example 22

Preparation of (S)-Pregabalin

A 0.2 liter reactor was loaded with 60 ml of water and 17.65 g of NaOH. The solution was cooled to from 10° to 15° C., and 15 g of 25 were added. Then, 15 g of Br$_2$ were added drop-wise over a period of 15 minutes, while maintaining the temperature at less than 20° C. The mixture was heated to 80° C. for 15 minutes, and then cooled to room temperature, i.e., about 20° to about 25° C. An aqueous 32 percent solution of HCl was added in an amount sufficient to provide a pH of 1. The solution was then divided to two portions.

Portion I was extracted with 37 ml of iso-butanol, the organic layer was separated, and Bu$_3$N was added in an amount sufficient to provide a pH of 4. The (S)-Pregabalin was precipitated, filtered, and washed with 10 ml of iso-butanol. After drying at 55° C. under vacuum, (S)-Pregabalin was obtained as white crystals in a 71 percent yield. Optical purity: 97.2 percent area by HPLC.

Portion II was extracted with 37 ml of pentanol, the organic layer was separated, and Bu$_3$N was added in an amount sufficient to provide a pH of 4. The (S)-Pregabalin was precipitated, filtered, and washed with 10 ml of pentanol. After drying at 55° C. under vacuum, (S)-Pregabalin was obtained as white crystals in a 73 percent yield. Optical purity: 93.1 percent area by HPLC.

Example 23

Preparation of (S)-Pregabalin

A 0.1 liter reactor was loaded with 60 ml of water and 17.6 g of NaOH. The solution was cooled to from 10° to 15° C., and 15 g of 25 were added. The mixture was stirred, and 15 g of Br$_2$ were added drop-wise over a period of 45 minutes, while maintaining the temperature at less than 20° C. The mixture was heated to 85° C. for 15 minutes, and then was cooled to about 20 to about 25° C. Then, 12.4 ml of H$_2$SO$_4$ were added drop-wise in an amount sufficient to lower the pH to 1, and the resulting solution was divided to two portions.

Portion I was extracted with 37 ml of iso-butanol. The organic layer was separated, and Bu$_3$N was added in an amount sufficient to provide a pH of 4, precipitating (S)-Pregabalin, which was filtered, and washed with 10 ml of iso-butanol. After drying at 55° C. under vacuum, (S)-Pregabalin was obtained as white crystals in a 63 percent yield. Optical purity: 99.1 percent area by HPLC.

Portion II was extracted with 37 ml of pentanol, the organic layer was separated, and Bu$_3$N was added in an amount sufficient to provide a pH of 4. The precipitated (S)-Pregabalin was filtered, and washed with 10 ml of pentanol. After drying at 55° C. under vacuum, (S)-Pregabalin was obtained as white crystals in a 61 percent yield. Optical purity: 96.6 percent area by HPLC.

Example 24

Preparation of (S)-Pregabalin

A 0.2 liter reactor was loaded with 60 ml of water and 17.65 g of NaOH. The resulting solution was cooled to from 10° to 15° C., and 15 g of 25 were added. Then, 15 g of Br$_2$ were added drop-wise over 15 minutes, while maintaining the temperature at less than 20° C. The mixture was heated to 80° C. for 15 minutes, and then cooled to room temperature, i.e., about 20 to about 25° C. Then, 75 ml of iso-butanol were added, and an aqueous 32 percent solution of HCl was added in an amount sufficient to provide a pH of 2. The organic phase was separated, and (S)-Pregabalin was precipitated after the addition of 14 ml of Bu$_3$N. The mixture was cooled to 2° C., and the solid was filtered, washed, and dried at 55° C. under vacuum, providing a 61 percent yield. Optical purity: 98.7 percent area by HPLC.

Example 25

Preparation of (S)-Pregabalin

A 0.2 liter reactor was loaded with 60 ml of water and 17.65 g of NaOH. The solution was cooled to from 10° to 15° C., and 15 g of 25 were added. Then, 15 g of Br$_2$ were added drop-wise over 15 minutes, while maintaining the temperature at less than 20° C. The mixture was heated to 80° C. for 15 minutes, and then cooled to room temperature, i.e., about 20 to about 25° C. Then 75 ml of pentanol were added, followed by an aqueous 32 percent of HCl in an amount sufficient to provide a pH of 2. The organic phase was separated, and (S)-Pregabalin was precipitated after the addition of 14 ml of Bu₃N. The mixture was then cooled to 2° C., and the solid was filtered, washed, and dried at 55° C. under vacuum, providing a 52 percent yield. Optical purity: 96.9 percent area by HPLC.

Example 26

Preparation of (S)-Pregabalin

A 0.2 liter reactor was loaded with 110 ml of water and 27.65 g of NaOH. The solution was cooled to from 10° to 15° C., and 23.5 g of 25 were added. Then, 23.5 g of Br₂ were added drop-wise over 15 minutes, while maintaining the temperature at less than 20° C. The mixture was heated to 80° C. for 15 minutes, and then cooled to room temperature, i.e., about 20 to about 25° C. An aqueous 32 percent solution of HCl was added in an amount sufficient to provide a pH of 2. The mixture was then extracted with 138 ml of iso-butanol, and the organic phase was separated. (S)-Pregabalin precipitated after the addition of diisopropylethyl amine in an amount sufficient to provide a pH of 4. The mixture was cooled to 2° C., and the solid was filtered, washed, and dried at 55° C. under vacuum, providing a 43 percent yield. Optical purity: 98.4 percent area by HPLC.

Example 27

Preparation of (S)-Pregabalin

A reactor (0.2 liter) was loaded with water (50 ml), NaOH (14.7 g). The solution was cooled to 10-15° C. and 25 (12.5 g) was added. Br₂ (12.5 g) was added dropwise (15 min) while keeping the temperature below 20° C. The mixture was heated to 80° C. for 15 and then cooled to room temperature. Iso-butanol was added (75 ml) then a 66 percent solution of H₂SO₄ was added to obtain a pH of 2. The organic phase was separated, distilled (to a volume of 50 ml), (S)-Pregabalin was precipitated after addition of Bu₃N (11.6 ml). The mixture was cooled to 2° C., and then the solid was filtered, washed, and dried at 55° C. under vacuum, providing a 81 percent yield. Optical purity: 98.9 percent area by HPLC.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

We claim:
1. A process for the preparation of (S)-Pregabalin, comprising:
a) combining a chiral amine of formula 23,

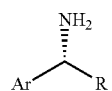
23 an organic solvent selected from at least one of aromatic hydrocarbons, ethers, halogenated hydrocarbons, alcohols, esters, alkanes, and ketones, and a base to obtain a mixture;
b) cooling the mixture to a temperature of about 10° C. to about −70° C.;
c) adding to the mixture 3-isobutyl glutaric anhydride of formula 22;

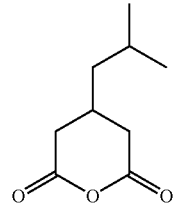
22 to obtain the compound of formula 24;
d) recovering the compound of formula 24 from the mixture;
e) converting the compound of formula 24 to a compound of the following formula 25

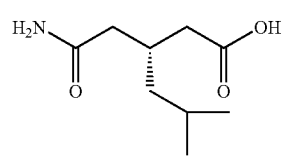
25 f) recovering the compound of formula 25;
g) combining the recovered compound of formula 25 with bromine, water, and an alkaline hydroxide to obtain a basic mixture;
h) heating the basic mixture to a temperature of about 60° C. to about 85° C.;
i) adding to the basic mixture a strong mineral acid to obtain an acidic mixture;
j) reacting the acidic mixture with a base to obtain (S)-Pregabalin, and

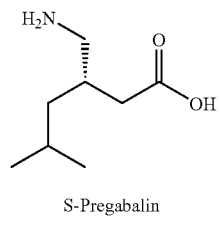

S-Pregabalin recovering (S)-Pregabalin;
wherein Ar is a $C_{6-10}$ aromatic group selected from the group consisting of naphthyl, phenyl, and substituted phenyl and R is straight or branched $C_{1-4}$ alkyl, ester or carboxylic acid.

2. The process according to claim 1, wherein the $C_{6-10}$ aromatic group is phenyl.

3. The process according to claim 1, wherein the R is straight or branched $C_{1-4}$ alkyl.

4. The process according to claim 3, wherein the straight or branched $C_{1-4}$ alkyl is methyl, ethyl, isopropyl, n-butyl, isobutyl or t-butyl.

5. The process according to claim 3, wherein the straight or branched $C_{1-4}$ alkyl is methyl or ethyl.

6. The process according to claim 3, wherein the straight or branched $C_{1-4}$ alkyl is methyl.

7. The process according to claim 1, wherein the substituted phenyl is a phenyl group substituted with at least one of alkoxy, halogen, alkyl, carboxylic acid, or ester.

8. The process according to claim 7, wherein the alkoxy substituted phenyl is methoxyphenyl.

9. The process according to claim 7, wherein the halogen substituted phenyl is chlorobenzene, bromobenzene or fluorobenzene.

10. The process according to claim 7, wherein the alkyl substituted phenyl is toluene or ethylbenzene.

11. The process according to claim 7, wherein the carboxylic acid substituted on the phenyl group is —COOH, —CH$_2$COOH, —CH(CH$_3$)COOH or —C(CH$_3$)$_2$COOH.

12. The process according to claim 7, wherein the ester substituted on the phenyl group is a methylester, ethylester, isopropyester, n-butylester, isobutyl ester, or t-butyl ester derivative of —COOH, —CH$_2$COOH, —CH(CH$_3$)COOH or —C(CH$_3$)$_2$COOH.

13. The process according to claim 1, wherein the chiral amine in step a) is a primary amine.

14. The process according to claim 13, wherein the primary amine is selected from a group consisting of: 1R,2S-Ephedrine, naphthyl-α-methyl ethylamine, Glycine methylester, methylbenzylamine and a chiral amino acid derivative.

15. The process according to claim 13, wherein the primary amine is methylbenzylamine.

16. The process according to claim 13, wherein the primary amine is (R)-methylbenzylamine.

17. The process according to claim 1, wherein the aromatic hydrocarbon is C$_{6-8}$ aromatic aromatic hydrocarbon.

18. The process according to claim 17, wherein the C$_{6-8}$ aromatic hydrocarbon is toluene or xylene.

19. The process according to claim 1, wherein the ether is C$_{3-6}$ ether.

20. The process according to claim 19, wherein the C$_{3-6}$ ether is selected from the group consisting of tert-butyl methyl ether, tetrahydrofuran, diisopropylether, and diethyl ether.

21. The process according to claim 1, wherein the halogenated carbon is a C$_{1-2}$ halogenated hydrocarbon.

22. The process according to claim 21, wherein the C$_{1-2}$ halogenated hydrocarbon is dichloromethane.

23. The process according to claim 1, wherein the alcohol is a C$_{1-4}$ alcohol.

24. The process according to claim 1, wherein the C$_{1-4}$ alcohol is selected from the group consisting of isopropyl alcohol, ethanol, methanol and n-butanol.

25. The process according to claim 1, wherein the ester is a C$_{3-6}$ ester.

26. The process according to claim 1, wherein the C$_{3-6}$ ester is ethyl acetate, isopropyl acetate, or isobutyl acetate.

27. The process according to claim 1, wherein the alkane is straight, branched or cyclic C$_{5-7}$.

28. The process according to claim 27, wherein the straight, branched or cyclic C$_{5-7}$ is either hexane or cyclohexane.

29. The process according to claim 1, wherein the ketone is a C$_{3-6}$ ketone.

30. The process according to claim 29, wherein the C$_{3-6}$ ketone is acetone, methyl isobutyl ketone, or methyl ethyl ketone.

31. The process according to claim 29, wherein the C$_{3-6}$ ketone is acetone.

32. The process according to claim 1, wherein the organic solvent in step a) is toluene.

33. The process according to claim 1, wherein the base in step a) is an organic base.

34. The process according to claim 32, wherein the organic base is a C$_{1-12}$ amine.

35. The process according to claim 34, wherein the C$_{1-12}$ amine is selected from the group consisting of diethyl amine, triethyl amine, di-n-propyl amine, di-isopropyl amine, tert-butylamine morpholine, piperidine, pyridine, and 4-dimethyl aminopyridine.

36. The process according to claim 34, wherein the organic base is 4-dimethyl aminopyridine.

37. The process according to claim 1, wherein the mixture in step b) is cooled to a temperature of about 0° C. to about −60° C.

38. The process according to claim 1, wherein the mixture in step b) is maintained at a temperature of about 0° C. to about −60° C. for about one hour to about two hours.

39. The process according to claim 1, wherein the recovered compound of formula 24 has an optical purity of at least about 93%.

40. The process according to claim 39, wherein the recovered compound of formula 24 has an optical purity of about 99% to about 100% area by HPLC.

41. The process according to claim 1, further comprising purifying the recovered compound 24 by crystallization from at least one organic solvent selected from the group consisting of esters, nitriles, ethers, C$_{4-6}$ straight, branched or cyclic hydrocarbons, C$_{6-10}$ aromatic hydrocarbons, and mixtures thereof.

42. The process according to claim 41, wherein the ester is C$_{3-6}$ ester.

43. The process according to claim 42, wherein the C$_{3-6}$ ester is ethyl acetate.

44. The process according to claim 41, wherein the nitrile is a C$_2$ nitrile.

45. The process according to claim 44, wherein the C$_2$ nitrile is acetonitrile.

46. The process according to claim 41, wherein the ether is a C$_{3-6}$ ether.

47. The process according to claim 46, wherein the C$_{3-6}$ ether is methyl t-butyl ether.

48. The process according to claim 41, wherein the C$_{6-10}$ substituted aromatic hydrocarbon is a C$_{7-9}$ aromatic hydrocarbon.

49. The process according to claim 48, wherein the C$_{7-9}$ aromatic hydrocarbon is toluene or xylene.

50. The process according to claim 41, wherein the mixtures are that of xylene and ethyl acetate, hexane and ethyl acetate, cyclohexane and ethyl acetate and toluene and ethyl acetate.

51. The process according to claim 50, wherein the mixture is that of toluene and ethyl acetate.

52. The process according to claim 1, wherein the compound of formula 24 is converted into the compound of formula 25 by a process comprising combining the compound of formula 24, water, an ether, ammonia and an alkali metal at a temperature of about 10° C. to about −78° C. to obtain a mixture of the compound of formula 25.

53. The process according to claim 52, wherein the compound of formula 24, water and ether are combined prior to the addition of the ammonia and alkali metal.

54. The process according to claim 53, wherein the ammonia and alkali metal are added to the compound of formula 24, water, and ether at a temperature of about 5° C. to about −40° C.

55. The process according to claim 52, wherein the ether is a C$_{3-6}$ ether.

56. The process according to claim 55, wherein the C$_{3-6}$ ether is tetrahydrofuran or dioxane.

57. The process according to claim 52, wherein the ammonia is an aqueous solution of ammonia.

58. The process according to claim 52, wherein the alkali metal is lithium or sodium.

59. The process according to claim 1, wherein the compound of formula 24 is converted into the compound of formula 25 by a process comprising combining the compound of formula 24 with concentrated sulfuric acid to obtain a mixture and maintaining the mixture at a temperature of about 0° C. to about 50° C. for about 10 hours to about 30 hours.

60. The process according to claim 1, wherein the alkaline hydroxide and water in step g) are combined to obtain a solution, prior to the addition of the compound of formula 25 and bromine.

61. The process according to claim 1, wherein the alkaline hydroxide in step g) is selected from a group consisting of sodium hydroxide, potassium hydroxide, lithium hydroxide and cesium hydroxide.

62. The process according to claim 61, wherein the alkali hydroxide in step g) is sodium hydroxide.

63. The process according to claim 60, wherein the compound of formula 25 is added to the solution of alkaline hydroxide and water at a temperature of about 5° C. to about 10° C.

64. The process according to claim 63, wherein the bromine is added to the solution of alkaline hydroxide and water after the addition of the compound of formula 25.

65. The process according to claim 64, wherein the bromine is added at a temperature of about 5° C. to about 10° C.

66. The process according to claim 1, wherein a $C_{4-8}$ alcohol is added to the basic mixture prior to the addition of the strong mineral acid in step i).

67. The process according to claim 66, wherein the $C_{4-8}$ alcohol is selected from the group consisting of butanol, iso-butanol, 2-butanol, pentanol and iso-pentanol.

68. The process according to claim 66, wherein the $C_{4-8}$ alcohol is iso-butanol.

69. The process according to claim 1, wherein the strong mineral acid is selected from the group consisting of $H_2SO_4$, HCl, HBr and $H_3PO_4$.

70. The process according to claim 1, wherein the strong mineral acid is HCl.

71. The process according to claim 1, wherein the addition of the strong mineral acid provides a two-phase system comprising an organic phase and an aqueous phase.

72. The process according to claim 71, wherein the base in step j) is added to the organic phase.

73. The process according to claim 1, wherein the base in step j) is an organic base.

74. The process according to claim 73, wherein the organic base is a secondary or tertiary amine.

75. The process according to claim 74, wherein the secondary amine is diisopropylamine or dipropylamine.

76. The process according to claim 74, wherein the secondary amine is diisopropylamine.

77. The process according to claim 74, wherein the tertiary amine is either tributyl amine or triethyl amine.

78. The process according to claim 74, wherein the tertiary amine is tributyl amine.

79. The process according to claim 1, wherein the base in step j) is an inorganic base.

80. The process according to claim 79, wherein the inorganic base is an alkali hydroxide or an alkali carbonate.

81. The process according to claim 80, wherein the alkali hydroxide is sodium hydroxide, potassium hydroxide, lithium hydroxide, or cesium hydroxide.

82. The process according to claim 80, wherein the alkali hydroxide is sodium hydroxide.

83. The process according to claim 80, wherein the alkali carbonate is sodium carbonate, sodium bicarbonate, or potassium carbonate.

84. The process according to claim 80, wherein the alkali carbonate is sodium carbonate.

85. The process according to claim 79, wherein the inorganic base is an alkali carbonate.

86. The process according to claim 1, wherein the base in step j) is tributylamine.

* * * * *

UNITED STATES PATENT AND TRADEMARK OFFICE
CERTIFICATE OF CORRECTION

| | | |
|---|---|---|
| PATENT NO. | : 7,470,812 B2 | |
| APPLICATION NO. | : 11/894855 | |
| DATED | : December 30, 2008 | |
| INVENTOR(S) | : Kansal et al. | |

It is certified that error appears in the above-identified patent and that said Letters Patent is hereby corrected as shown below:

Column 28
Claim 1 Line 13, change "the compound of" to --a compound of--
Claim 1 Line 30, change "an alkaline hydroxide" to --an alkali hydroxide--

Column 29
Claim 12 Line 13, change "isopropyester" to --isopropylester--
Claim 14 Line 19, change "a group" to --the group--
Claim 17 Line 27, change "aromatic aromatic hydrocarbon" to --aromatic hydrocarbon--
Claim 21 Lines 36-37, change "halogenated carbon" to --halogenated hydrocarbon--
Claim 23 Line 42, change "claim 1" to --claim 23--
Claim 26 Line 47, change "claim 1" to --claim 25--
Claim 34 Line 66, change "claim 32" to --claim 33--

Column 30
Claim 35 Line 4, change "butylamine morpholine" to --butylamine, morpholine--
Claim 41 Line 23, change "nitrites" to --nitriles--
Claim 48 Line 39, change "substituted aromatic hydrocarbon" to --aromatic hydrocarbon--
Claim 50 Line 45, change "and toluene" to --or toluene--

Column 31
Claim 60 Lines 9-10, change "the alkaline hydroxide" to --the alkali hydroxide--
Claim 61 Lines 13-14, change "the alkaline hydroxide" to --the alkali hydroxide--
Claim 61 Line 14, change "a group" to --the group--
Claim 63 Lines 20-21, change "solution of alkaline hydroxide" to --solution of alkali hydroxide--
Claim 64 Line 24, change "solution of alkaline hydroxide" to --solution of alkali hydroxide--
Claim 67 Line 31, change "C4-$_8$" to --C$_{4-8}$--

Signed and Sealed this
Thirtieth Day of August, 2011

David J. Kappos
*Director of the United States Patent and Trademark Office*